US011517630B2

(12) United States Patent
Mulligan et al.

(10) Patent No.: US 11,517,630 B2
(45) Date of Patent: Dec. 6, 2022

(54) METHODS AND COMPOSITIONS FOR REGULATING GENE EXPRESSION

(71) Applicant: Children's Medical Center Corporation, Boston, MA (US)

(72) Inventors: Richard Mulligan, Cambridge, MA (US); George J. Murphy, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 986 days.

(21) Appl. No.: 16/200,974

(22) Filed: Nov. 27, 2018

(65) Prior Publication Data

US 2019/0151475 A1    May 23, 2019

Related U.S. Application Data

(62) Division of application No. 13/736,748, filed on Jan. 8, 2013, now Pat. No. 10,159,754, which is a division of application No. 12/083,743, filed as application No. PCT/US2006/040607 on Oct. 17, 2006, now abandoned.

(60) Provisional application No. 60/727,327, filed on Oct. 17, 2005.

(51) Int. Cl.
| | |
|---|---|
| *C12N 15/85* | (2006.01) |
| *A61K 48/00* | (2006.01) |
| *C12Q 1/6813* | (2018.01) |
| *C12N 15/86* | (2006.01) |
| *A61K 31/7036* | (2006.01) |
| *A61K 35/12* | (2015.01) |

(52) U.S. Cl.
CPC ...... *A61K 48/0066* (2013.01); *A61K 31/7036* (2013.01); *A61K 35/12* (2013.01); *C12N 15/85* (2013.01); *C12N 15/86* (2013.01); *C12Q 1/6813* (2013.01)

(58) Field of Classification Search
None
See application file for complete search history.

(56) References Cited

U.S. PATENT DOCUMENTS

| | | | |
|---|---|---|---|
| 5,663,152 A | 9/1997 | Hayano et al. | |
| 2002/0086427 A1 | 7/2002 | Leiden et al. | |
| 2003/0049666 A1 | 3/2003 | Howard et al. | |
| 2004/0009126 A1 | 1/2004 | Pilkiewicz et al. | |
| 2004/0115787 A1 | 6/2004 | Peltz | |
| 2005/0233327 A1 | 10/2005 | Welch et al. | |
| 2006/0167263 A1 | 7/2006 | Wilde et al. | |
| 2007/0224635 A1 | 9/2007 | Bouquin | |
| 2011/0269120 A1 | 11/2011 | Yim | |
| 2016/0122771 A1 | 5/2016 | Dhadialla | |
| 2016/0208280 A1 | 7/2016 | Fire | |

FOREIGN PATENT DOCUMENTS

| | | |
|---|---|---|
| WO | WO 2004/009533 | 1/2004 |
| WO | WO 2006/044682 | 4/2006 |

OTHER PUBLICATIONS

Bidou et al. Gene Therapy 11:619-627, Feb. 2004 (Year: 2004).*
Kafri et al. Molecular Therapy 1(6):516-521, 2000 (Year: 2000).*
Liu et al Gene 203:141-148, 1998 (Year: 1998).*
Howard et al. Ann Neurol 48:164-169, 2000 (Year: 2000).*
Howard et al., "Readthrough of dystrophin stop condon mutations induced by aminoglycosides," Ann. Neurol., 55, 3:422-426 (2004).
International Preliminary Report on Patentability issued in co-pending International Application No. PCT/US2006/040607 dated Apr. 23, 2008.
International Search Report issued in co-pending International Application No. PCT/US2006/040607 dated Nov. 6, 2007.
Keeling et al. (2004) Leaky termination at premature stop codons antagonizes nonsense-mediated mRNA decay in S. cerevisiae, RNA, vol. 10, No. 4, pp. 691-703.
Manuvakhova et al., "Aminoglycoside antibiotics mediate context-dependent suppression of termination codons in a mammalian translation system," RNA, 6:1044-1055 (2000).
Murphy et al., "Exogenous control of mammalian gene expression via modulation of translational termination," Nature Medicine, 12(9): 1093-1099 (2006).
NCBI, "*Homo sapiens* dystrophin (DMD), transcript variant Dp427m, mRNA," www.ncbi.nlm.nih.gov/nuccore/NM_004006.2 pp. 1-20.
Parrott et al., "Apoc-II-Paris-2 A Premature termination mutation in the signal peptide of APOC-II resulting in the familial chylomicronemia syndrome," Journal of Lipid Research, 33(3): 361-367 (1992).
Written Opinion of the International Searching Authority issued in co-pending International Application No. PCT/US2006/040607 dated Nov. 6, 2007.

* cited by examiner

*Primary Examiner* — Marcia S Noble

(74) *Attorney, Agent, or Firm* — Fish & Richardson P.C.

(57) ABSTRACT

In certain embodiments, the disclosure relates to compositions and methods relating to a translation-based gene regulation system that functions in mammalian cells. In certain specific embodiments, the disclosure relates to methods of regulating gene expression via modulating translation termination.

13 Claims, 5 Drawing Sheets

Specification includes a Sequence Listing.

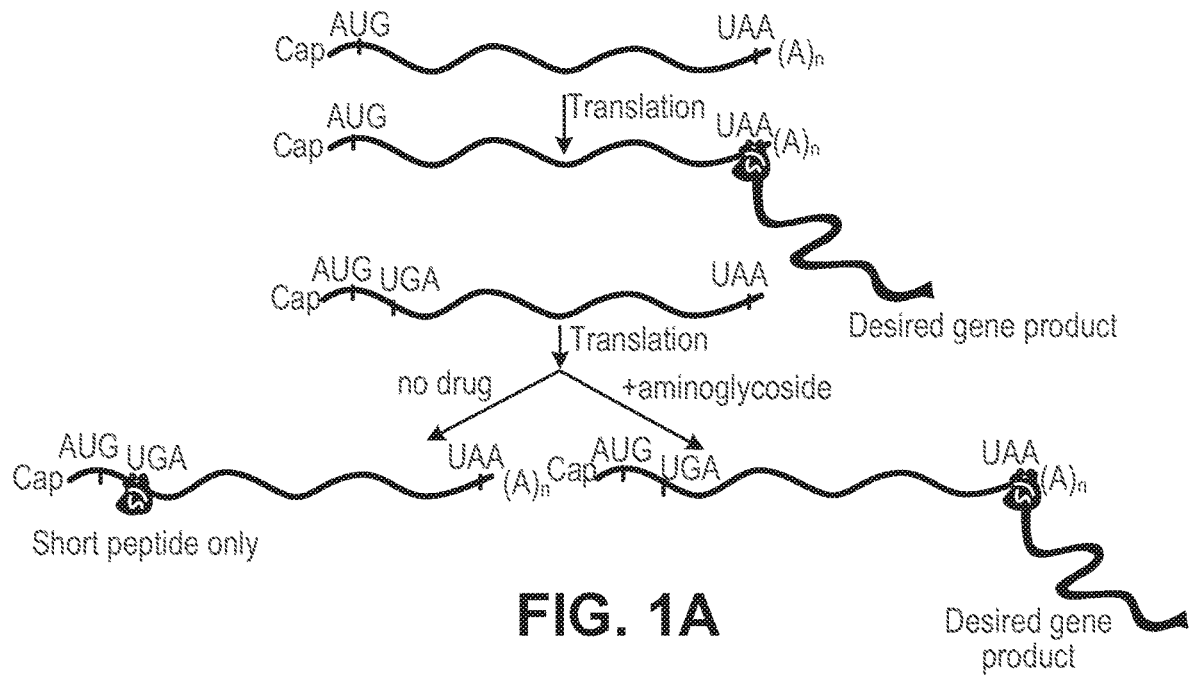
FIG. 1A
FIG. 1B
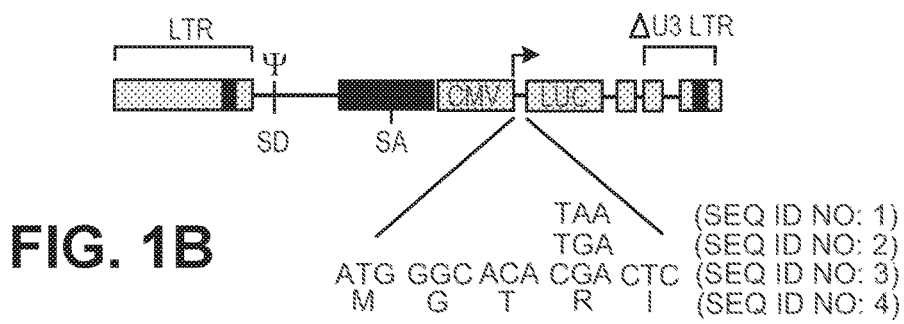
FIG. 1C

METHODS AND COMPOSITIONS FOR REGULATING GENE EXPRESSION

CROSS REFERENCE TO RELATED APPLICATIONS

This application claims the benefit of the filing date of U.S. Provisional Application 60/727,327, filed Oct. 17, 2005. The entire teachings of the referenced provisional application are expressly incorporated by reference herein.

FUNDING

This invention was made with government support under Grant Number NIH 5PO-HL54785 awarded by National Institutes of Health. The government has certain rights in the invention.

BACKGROUND OF THE INVENTION

The ability to exogenously control the expression of genes in mammalian cells has been a powerful tool of biomedical research. In particular, gene regulation technology has played a central role in efforts to understand the role of specific gene products in fundamental biological processes and in both normal development and disease states. It is likely that this form of genetic technology will continue to have impact in a variety of areas of basic research and may enable new therapeutic paradigms, such as the regulated delivery of protein therapeutics. The technology may also have significant future impact upon the safety of gene therapy strategies.

To date, most of the gene regulation systems commonly utilized are based on the control of transcription. Despite their considerable utility, these systems possess some significant limitations due to their reliance on chimeric transcriptional transactivators and specialized promoter elements. Such limitations include the requirement for co-introduction of genes encoding the relevant transcriptional transcriptional transactivator along with the gene to be regulated, and the inability to provide for the "on-off" regulation of a gene in the context of its own endogenous transcriptional control elements.

Thus, there is a need for developing a novel gene regulation system that does not rely on the control of transcription.

SUMMARY OF THE INVENTION

The present invention relates to compositions and methods for regulating translation of a target protein by suppressing a nonsense mutation which has been introduced into a nucleic acid encoding the target protein.

In certain embodiments, the present invention provides a method for inducing expression of a target protein in a host cell. Such method comprises contacting the host cell with an effective amount of an agent, wherein the host cell comprises a nucleic acid encoding a target protein, wherein the nucleic acid is operably linked to a promoter and has been modified to contain at least one nonsense mutation downstream to and in close proximity of the start codon that initiates translation of the target protein, and wherein the agent suppresses the nonsense mutation. A preferred host cell is a mammalian cell (e.g., a human cell). Examples of the agent that suppresses the nonsense mutation include, but are not limited to, an aminoglycoside antibiotic or an analog thereof, such as G418, and an acetylamino benzoic acid compound or a derivative thereof, such as 3-[2-(4-tert-butyl-phenoxyl)-acetylamino]-benzoic acid and 3-{2-[4-(1,1-dimethyl-propyl)-phenoxyl]acetylamino}-benzoic acid. Optionally, the number of codons between the nonsense mutation and the start codon is selected from: 0, 1, 2, 3, 4, and 5. In certain case, the target protein is a secreted protein and the nonsense mutation is introduced in a region of the nucleic acid which encodes a signal peptide. Optionally, the nucleic acid is present in the genome of the cell or present on a vector (e.g., a viral vector).

In certain embodiments, the present invention provides a recombinant polynucleotide molecule comprising a nucleic acid encoding a target protein, wherein the nucleic acid is operably linked to a promoter and has been modified to contain at least one nonsense mutation downstream to and in close proximity of the start codon that initiates translation of the target protein. Optionally, the number of codons between the nonsense mutation and the start codon is selected from: 0, 1, 2, 3, 4, and 5. In certain case, the target protein is a secreted protein and the nonsense mutation is introduced in a region of the nucleic acid which encodes a signal peptide. Optionally, the nucleic acid is present in the genome of the cell or present on a vector (e.g., a viral vector).

In certain embodiments, the present invention provides a host cell comprising a polynucleotide molecule of the invention, such as a polynucleotide molecule comprising a nucleic acid encoding a target protein, wherein the nucleic acid is operably linked to a promoter and has been modified to contain at least one nonsense mutation downstream to and in close proximity of the start codon that initiates translation of the target protein. Preferably, the cell is a mammalian cell (e.g., a human cell). Optionally, the cell further comprises an agent which suppresses the nonsense mutation.

In certain embodiments, the present invention provides a transgenic non-human animal, comprising a host cell of the invention. For example, the transgenic non-human animal is a mouse which contains a nucleic acid encoding a target protein, wherein the nucleic acid is operably linked to a promoter and has been modified to contain at least one nonsense mutation downstream to and in close proximity of the start codon that initiates translation of the target protein.

In certain embodiments, the present invention provides a recombinant vector comprising: (a) a promoter; (b) a nucleic acid encoding a linker peptide, wherein the nucleic acid is operably linked to the promoter, and wherein the nucleic acid has been modified to contain at least one nonsense mutation located downstream to and in close proximity of the start codon that initiates translation of the linker peptide; and (c) at least one cloning site downstream to the nucleic acid for introducing a target nucleic acid sequence which encodes a target protein to be fused in frame to the carboxyl terminus of the linker peptide. For example, the linker peptide is a signal peptide (e.g., a native or a non-native signal peptide of the target protein).

In certain embodiments, the present invention provides a kit for regulating gene expression. The subject kit comprises a vector comprising: (a) a promoter; (b) an nucleic acid encoding a linker peptide, wherein the nucleic acid is operably linked to the promoter, and wherein the nucleic acid has been modified to contain at least one nonsense mutation located downstream to and in close proximity of the start codon that initiates translation of the linker peptide; and (c) at least one cloning site downstream to the nucleic acid for introducing a target nucleic acid sequence which encodes a target protein to be fused in frame to the carboxyl terminus of the linker peptide. For example, the linker peptide is a signal peptide (e.g., a native or a non-native signal peptide of the target protein). Optionally, the kit further comprises an agent that suppresses a nonsense mutation. Examples of the agent that suppresses the nonsense mutation include, but are not limited to, an aminoglycoside antibiotic or an analog thereof, such as G418, and an acetylamino benzoic acid compound or a derivative thereof, such as 3-[2-(4-tert-butyl-phenoxyl)-acetylamino]-benzoic acid and 3-{2-[4-(1,1-dimethyl-propyl)-phenoxyl]acetylamino}-benzoic acid.

In certain embodiments, the present invention provides a method for identifying a nucleic acid construct having a desired biological activity from a population of nucleic acid constructs. In this method, a population of candidate nucleic acid constructs is produced, wherein each of the candidate nucleic acid construct is cloned into the multiple cloning sites of the vector which comprises: (a) a promoter; (b) an nucleic acid encoding a linker peptide, wherein the nucleic acid is operably linked to the promoter, and wherein the nucleic acid has been modified to contain at least one nonsense mutation located downstream to and in close proximity of the start codon that initiates translation of the linker peptide; and (c) at least one cloning site downstream to the nucleic acid for introducing a target nucleic acid sequence which encodes a target protein to be fused in frame to the carboxyl terminus of the linker peptide. The population of candidate nucleic acid constructs is expressed in a test cell. If a nucleic acid construct, when expressed in the test cell in the presence of an agent that suppresses the nonsense mutation, produces a desired biological activity, then a nucleic acid construct having a desired biological activity is identified from a population of nucleic acid constructs.

In certain embodiments, the present invention provides a method for producing a transgenic nonhuman animal in which the expression of a target protein can be modulated by an agent that suppresses a nonsense mutation. Such method comprises introducing a DNA construct into a germ cell of a nonhuman animal or a germ cell of an ancestor of said animal, wherein said DNA construct comprises a nucleic acid encoding the target protein, wherein the nucleic acid is operably linked to a promoter and has been modified to contain at least one nonsense mutation downstream to and in close proximity of the start codon that initiates translation of the target protein. In certain embodiments, the present invention provides a transgenic non-human animal generated by such method.

In certain embodiments, the present invention provides a method for producing a transgenic non-human animal in which the translation of a target protein can be modulated by an agent that suppresses a nonsense mutation. Such method comprises: (a) providing a DNA molecule comprising a nucleic acid sequence flanked at 5' and 3' ends by additional polynucleotide sequences of sufficient length for homologous recombination between the DNA molecule and a chromosomal endogenous target region, wherein the nucleic acid has been modified to contain at least one nonsense mutation downstream to and in close proximity of the start codon that initiates translation of the target protein; (b) introducing the DNA molecule of (a) into a population of embryonic stem cells under conditions appropriate for homologous recombination between the DNA molecule and the chromosomal endogenous target region to occur, resulting in embryonic stem cells in which the DNA molecule of (a) is integrated into the chromosomal endogenous target region; (c) selecting an embryonic stem cell in which the DNA molecule of (a) is integrated at the chromosomal endogenous target region; (d) implanting the embryonic stem cell selected from (c) into a blastocyst; and (e) implanting the blastocyst into a pseudopregnant foster mother, thereby producing a non-human transgenic animal in which the translation of the target protein can be modulated by an agent that suppresses the nonsense mutation. A preferred non-transgenic animal is a mammal (e.g., mouse). Optionally, the DNA molecule has integrated into one or two copies of the chromosomal endogenous target region. In certain embodiments, the present invention provides a transgenic non-human animal generated by such method.

In certain embodiments, the present invention provides a method for inducing expression of a target gene in a subject transgenic non-human animal of the invention. Such method comprises administering to the transgenic non-human animal an agent that suppresses the nonsense mutation. Examples of the agent that suppresses the nonsense mutation include, but are not limited to, an aminoglycoside antibiotic or an analog thereof, such as G418, and an acetylamino benzoic acid compound or a derivative thereof, such as 3-[2-(4-tert-butyl-phenoxyl)-acetylamino]-benzoic acid and 3-{2-[4-(1,1-dimethyl-propyl)-phenoxyl]acetylamino}-benzoic acid. In certain cases, the agent is administered in a tissue-specific manner such that expression of the target gene is induced in a tissue-specific manner. In other cases, the agent is administered in a temporal specific manner such that expression of the target gene is induced in a temporal-specific manner.

In certain embodiments, the present invention provides a method for identifying an agent that suppresses a nonsense mutation. Such method comprises (a) providing a test host cell which contains a polynucleotide molecule comprising a nucleic acid encoding a target protein, wherein the nucleic acid is operably linked to a promoter and has been modified to contain at least one nonsense mutation downstream to and in close proximity of the start codon that initiates translation of the target protein; (b) providing a control host cell comprising a wild type nucleic acid encoding the target protein expressed under an appropriate promoter and the expression of the target protein is at wild type level; (c) contacting the test host cell and the control host cell with a candidate agent; and (d) assaying for the level of the target protein in the test host cell and in control host cell. If the candidate agent induces translation of the target protein in the test host cell to a significant level, the candidate agent is an agent that suppresses the nonsense mutation. Optionally, the target protein is fused to a reporter moiety and the expression of the reporter moiety is assayed. A preferred host cell is a mammalian cell. In certain cases, the number of codons between the nonsense mutation and the start codon is selected from; 0, 1, 2, 3, 4 and 5. In certain specific embodiments, the target protein is a secreted protein, and the nonsense mutation is introduced in a region of the nucleic acid which encodes a signal peptide.

In certain embodiments, the present invention provides a method for identifying an agent that suppresses a nonsense mutation in vivo. Such method comprises (a) providing a transgenic nonhuman animal which contains a polynucleotide molecule comprising a nucleic acid encoding a target protein, wherein the nucleic acid is operably linked to a promoter and has been modified to contain at least one nonsense mutation downstream to and in close proximity of the start codon that initiates translation of the target protein; (b) providing a control nonhuman animal which contains a wild type nucleic acid encoding the target protein expressed under an appropriate promoter and the expression of the target protein is at wild type level; (c) administering to the transgenic animal and the control animal a candidate agent;

and (d) assaying for the level of the target protein the transgenic animal and the control animal. If the candidate agent induces translation of the target protein in the transgenic animal to a significant level, the candidate agent is an agent that suppresses the nonsense mutation. Optionally, the target protein is fused to a reporter moiety and the expression of the reporter moiety is assayed. A preferred host cell is a mammalian cell. In certain cases, the number of codons between the nonsense mutation and the start codon is selected from: 0, 1, 2, 3, 4 and 5. In certain specific embodiments, the target protein is a secreted protein, and the nonsense mutation is introduced in a region of the nucleic acid which encodes a signal peptide.

In certain embodiments, the present invention provides a method of inducing expression of a target gene in an individual. The method can be carried out, for example, by introducing cells containing a DNA construct described herein into an individual or by introducing a vector or DNA construct described herein into an individual. In one embodiment, the method comprises (a) obtaining cells from the individual; (b) maintaining the cells under conditions appropriate for cell growth and cell division; (c) introducing into the cells of step (b) a DNA construct comprising a nucleic acid encoding a target protein, wherein the nucleic acid is operably linked to a promoter and has been modified to contain at least one nonsense mutation downstream to and in close proximity of the start codon that initiates translation of the target protein; (d) returning the cells produced in step (e) to the individual; and (e) administering to the individual an agent that suppresses the nonsense mutation. Alternatively, a DNA construct comprising a nucleic acid encoding a target protein, wherein the nucleic acid is operably linked to a promoter and has been modified to contain at least one nonsense mutation downstream to and in close proximity of the start codon that initiates translation of the target protein, can be introduced into an individual in whom induction of expression of a target gene is desired. The target protein to be induced by the method can be, for example, a therapeutic protein.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

FIGS. 1A-1C show design features of translation-based system for gene regulation. FIG. 1A shows a schematic diagram of gene regulation strategy. Relative positions of cap and polyadenylation sequences and initiation and termination codons within mRNA are shown as well as products of translation in presence and absence of aminoglycoside. Brown structure and green 'ribbon' denote ribosome translating mRNA and nascent polypeptides produced, respectively. FIG. 1B shows a sequence configuration of initiation and termination codons used to generate initial luc fusion proteins are shown, as well as structure of lentiviral vector used for studies. FIG. 1C shows levels of luc reporter gene expression obtained with additional configurations of nonsense codon sequences and adjacent sequences. Uninduced and induced refer to levels of luc achieved in absence and presence of aminoglycoside; the values are expressed as the % of luc activity achieved in cells carrying the luc construct possessing no nonsense mutations and not exposed to drug and represent the average of five independent determinations. Fold-induction refers to the ratio of induced to uninduced levels of activity.

FIG. 3B indicates induction (by 3-[2-(4-tert-butyl-phenoxyl)-acetylamino]-benzoic acid. FIG. 3C indicates induction by 3-{2-[4-(1,1-dimethyl-propyl)-phenoxyl] acetylamino}-benzoic acid. Both compounds were purchased from Chembridge.

DETAILED DESCRIPTION OF THE INVENTION

Figure 2A:
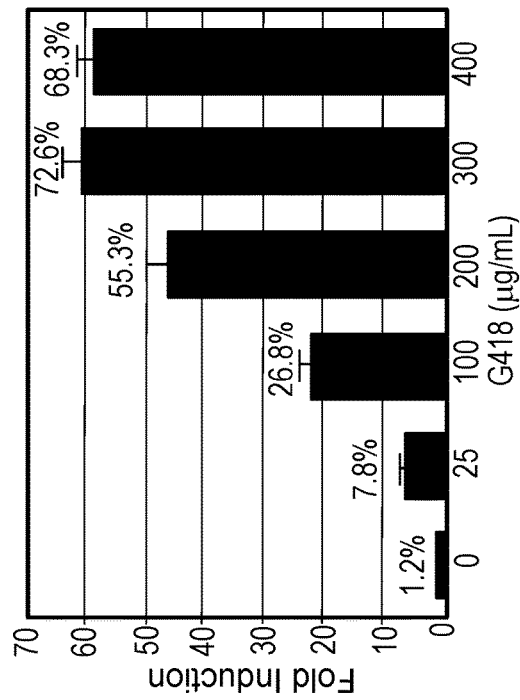
FIGS. 2A-2C show data demonstrating aminoglycoside-induced suppression of translational termination can be used to regulate gene expression in cultured cells (panels A and B) Expression of luc in FG293 cells infected with lentiviral vectors encoding either the WT (panel A) or mutant (panel B) luciferase fusion product (see Results), as a function of aminoglycoside concentration. Luc activity is measured in relative light units (RLU); % of levels of luc activity achieved with WT luciferase fusion product are indicated for each drug concentration. (C) Kinetics of induction of luc gene expression in FG293 cells infected with the lentiviral vector encoding the mutant luc fusion product. Cells were exposed to a constant concentration of G418 (200 μg/ml) and were analyzed for luc expression at hourly intervals. % WT luc activity is indicated for each time point, and represents the average of five independent determinations.

In certain embodiments, the present invention provides novel compositions and methods of gene regulation that relies on the control of translational termination. Applicants have shown that, using the novel gene regulation system (e.g., compositions and methods) of the invention, significant level of induction of expression of gene products can be obtained. Such induction of expression is rapid, and regulation of expression can be achieved in a variety of in vitro and in vivo contexts. Applicants have also described several small molecule agents that effectively suppress nonsense mutation mediated translational termination in vitro and in vivo. The gene regulation system of the present invention is simple to implement, and allow the regulation of gene expression to occur in the context of the normal endogenous control elements of a target gene. Certain examples of the target genes include a mammalian gene which encodes a secreted protein.

For example, the gene regulation system of the present invention relates to a method for inducing expression of a target protein in a host cell. Such method comprises contacting the host cell with an effective amount of an agent, wherein the host cell comprises a nucleic acid encoding a target protein, wherein the nucleic acid is operably linked to a promoter and has been modified to contain at least one nonsense mutation downstream to and in close proximity of the start codon that initiates translation of the target protein, and wherein the agent suppresses the nonsense mutation.

The term "expression," as used herein, refers to the biological process of producing an active polypeptide from the nucleic acid molecule or gene that encodes it. The term is intended to encompass some or all of the steps of normal genetic expression including, transcriptional initiation, transcription, transcript processing, translation, and post-translational processing.

The term "nonsense mutation" or "stop codon mutation," as used herein, is intended to refer to a mutation that results in the introduction of a non-naturally-occurring stop codon in a coding region of a target nucleic acid. The term "coding region" refers to nucleotide sequence of a gene which specifies the curious for translation into proteins, e.g., the region that codes for the amino acids. Coding region sequences are to be distinguished from other non-coding sequences, for example, 5' untranslated regions, 3' untranslated regions, and introns.

The term "suppress a nonsense mutation," as used herein, is intended to encompass counteracting or overcoming, the effect of the nonsense mutation, either partially or entirely, such that translation of a target protein from its encoding nucleic acid is partially or fully restored. As a result, expression of a target protein is partially or fully restored.

Nonsense Mutations and Nucleic Acid Molecules Comprising Nonsense Mutations

In certain embodiments, the present invention relates to a recombinant polynucleotide molecule comprising a nucleic acid encoding a target protein, wherein the nucleic acid is operably linked to a promoter and has been modified to contain at least one nonsense mutation downstream to and in close proximity of the start codon that initiates translation of the target protein. The term "modified" refers to the deliberate modification of a coding region of a target nucleic acid (e.g., a gene or a portion thereof) and is not intended to encompass naturally occurring nonsense mutations that may exist in the a target nucleic acid. In certain case, the polynucleotide molecule is present in the genuine of a cell. Alternatively, the polynucleotide molecule is present on a vector (e.g., a viral vector).

Optionally, the nonsense mutation is positioned close to the beginning of the target protein coding sequence. To illustrate, the number of codons between the nonsense mutation and the start codon is selected from: 0, 1, 2, 3, 4, and 5. In some cases, the nonsense mutation is introduced into a target nucleic acid with some additional sequences flanking the nonsense mutation. For example, a naturally occurring nonsense mutation in the human Apo CII gene (see, e.g., FIG. 1B) can be introduced into a target nucleic acid. Alternatively, artificially designed nonsense mutation-containing nucleotide sequence may be introduced into a target nucleic acid. Optionally, a nonsense mutation is positioned in a target nucleic acid in such a way that an mRNA containing the nonsense mutation is not subject to nonsense-mediated mRNA decay (NMD).

In certain specific embodiments, the present invention relates to regulation of expression of a target protein which is a secreted protein. For example, the nonsense mutation is introduced in a region of the nucleic acid which encodes a signal peptide of the secreted protein such that the structure of the mature protein is not affected by the introduction of the nonsense mutation.

In certain specific embodiments, the present invention provides a recombinant vector comprising: (a) a promoter; (b) an nucleic acid sequence encoding a linker peptide, wherein the nucleic acid is operably linked to the promoter, and wherein the nucleic acid has been modified to contain at least one nonsense mutation located downstream to and in close proximity of the start codon that initiates translation of the linker peptide; and (c) at least one cloning site downstream to the nucleic acid for introducing a target nucleic acid sequence which encodes a target protein to be fused in frame to the carboxyl terminus of the linker peptide. As used herein, a "linker peptide" refers to a peptide that is fused at the carboxyl terminus of a target protein and does not contribute to the functions of the target protein. Preferably, the linker peptide can be readily removed from the target protein such as by enzyme digestion or post-translational cleavage. Examples of such linker peptide include, but are not limited to, signal peptides and labeling peptides (e.g., histidine tag, Myc, Fc, GST). When the linker peptide is a signal peptide, it is understood that the signal peptide can be a native or a non-native signal peptide of the target protein.

It is known in that art that translation is almost always initiated at a methionine codon (AUG) codon, and the end of translation is signaled by one of three possible stop codons (UAG, UAA, UGA). In the present invention, expression of a target protein is perturbed by introducing at least one nonsense mutation (e.g., UAG, UAA, UGA) into a coding sequence to perturb normal translation of the target protein. For example, one of the three stop codons (i.e., UAG, UGA, UAA) is created from a single, double, or triple nucleotide mutation in the nucleotides of one or more selected amino acid-specifying codons. Genes that have such mutations introduced into their coding region, upon translation, produce gene products that are terminated at the codon of the mutation. Optionally, the nonsense mutation is introduced in close proximity of the start codon, resulting in no expression of the target protein or a truncated inactive version of the target protein. Preferably, introduction of the nonsense mutation does not result in alterations of the kinetics of messenger RNA stability.

Methods of introducing a nonsense mutation in a target nucleic acid are known in the art. Some or all of the nucleotide sequence of the coding region of the desired gene must be known to allow for design of the appropriate introduced mutation(s). For desired genes in which the sequence of some or all of the coding region is not known, standard DNA sequencing methods can be used to obtain the sequence of some or all of the coding region of the gene.

For example, the nonsense mutations of the invention are introduced into a desired gene through methods of directed mutagenesis. As used herein, the term "directed mutagenesis" (also referred to as site-directed mutagenesis) encompasses methods of introducing a specific and predetermined mutation into a known nucleotide sequence. Furthermore, as used herein, the term "directed mutagenesis" implies that some or all of the nucleotide sequence that is intended to be mutated has been determined or is known. For example, one or more specific mutations may be introduced into the coding region of a desired gene by one skilled in the art using directed mutagenesis methods involving specifically designed oligonucleotides, e.g., oligonucleotide-directed mutagenesis. These methods typically involve the introduction of the desired gene into a vector that can be reliably replicated from an oligonucleotide primer. Oligonucleotide primers with one or more nucleotide mismatches inside the hybridizing region (i.e., the region that hybridizes to the desired gene) can be readily designed and used by one skilled in the art to introduce mutations of the invention into a desired gene by standard recombinant DNA techniques known in the art.

In certain specific embodiments, a viral vector replication system is used for oligonucleotide-directed mutagenesis, e.g., an M13 viral vector. Methods for introducing mutations of the invention with M13 and other viral vectors are readily available in the art (see, for example, Kunkel, 1985, PNAS U.S.A. 82:488-492; Kunkel et al, 1987, Meth. Enzymol., 154; 367-382). In other specific embodiments, a bacterial plasmid replication system is used, in which the desired gene is introduced into the bacterial plasmid and the mutation(s) of the invention is deliberately introduced into the desired gene with oligonucleotide primers containing one or more mismatches at preselected nucleotide positions. Several such systems have been described that can be readily used by one skilled in the art (see, for example, Deng and Nikoloff, 1992, Anal. Biochem. 200:81-88; Nikoloff et al, 1996, 58:455-468).

In certain embodiments of the invention, mutations of the invention may be introduced into desired genes during amplification with PCR (polymerase chain reactions), also referred to as PCR-mediated mutagenesis. A number of PCR-based methods to deliberately introduce mutations into a desired gene are available in the art and can be used in the invention (see, for example, Ausubel et al, Current Protocols in Molecular Biology, John Wiley & Sons, 1995). These methods generally involve the use of oligonucleotide primers for PCR amplification reactions that contain one or more nucleotide mismatches within the hybridizing region (i.e., the region of hybridization with the desired gene).

In certain embodiments of the invention, mutations of the invention may be introduced into a desired gene through methods of non-directed mutagenesis. As used herein, the term "non-directed mutagenesis" refers to any method of introducing mutations randomly into the desired gene in a replicable biological system and having a means of screening resultant nucleic acids and to select and use the one(s) which contains a mutation of the invention in a desired gene. Such non-directed mutagenesis can be accomplished through a variety of means, the example, by exposure of the gene and/or the replicable biological system in which it is propagated, to mutagenic conditions, e.g., irradiation, chemical mutagens and the like. Other methods available to one skilled in the art include any method involving enzymatic replication of nucleic acid, for example with a polymerase or a replicas, whereby the intrinsic replication error rate of the enzyme is able to accomplish non-directed mutagenesis. As used herein, "screening" of the resultant nucleic acids to find a desired gone with a mutation of the invention includes methods for determining nucleotide sequences, e.g., sequencing analysis. In addition, the term "screening" also includes methods for determining amino acid sequences of protein, e.g. microsequencing. The term "screening" furthermore includes biological assays that can discern mutations of the invention in a desired gene, in particular mutations that result in the production of an inactive (partially or completely) gene product upon translation of the desired gene. Depending on which desired gene is selected, the ordinarily skilled artisan can select an appropriate known biological assay by which to screen randomly generated mutants to thereby select mutants that result in the production of an inactive (partially or completely) gene product upon translation of the desired gene.

In still another embodiment, a mutation of the invention is introduced into a desired gene that is present within the genome of a eukaryotic cell (i.e., an endogenous gene) by manipulation of the endogenous gene sequence, preferably by homologous recombination. Methods of using homologous recombination to alter the sequence of an endogenous eukaryotic gene are well known in the art and can be applied to deliberately introduce one or more mutations or the invention into a desired endogenous eukaryotic gene. Such methods typically involve construction of a gene targeting vector comprising at least a portion of the endogenous gene sequence, introduction of the targeting vector into a eukaryotic cell containing the endogenous desired gene and culture under conditions sufficient to allow for homologous recombination between the targeting vector and the endogenous gene, followed by screening of clones for ones in which the endogenous gene has undergone homologous recombination with the targeting vector using standard recombinant DNA techniques. To introduce one or more mutations into the endogenous gene, the targeting vector includes at least a portion of the endogenous gene sequence into which the mutation(s) has been introduced, flanked by wildtype sequences of the endogenous gene to facilitate homologous recombination between the targeting vector and the endogenous gene.

The Examples below further describe in detail how to introduce nonsense mutations into various target nucleotide sequences including human growth hormone (hGH) gene and how to design and select appropriate nonsense mutations that can be used for effectively inducing expression of a target protein in the presence of an agent that suppresses the nonsense mutation.

Vectors, Cell Lines, and Transgenic Animals

In certain embodiments, the present invention relates to methods of inserting at least one nonsense mutation into an endogenous target gene in a cell, or into an exogenous target gene to be introduced into a cell by a vector. In either case, necessary elements (e.g., promoters) are present for the transcription of the modified target gene which contains the nonsense mutation. For example, such modified target gene is placed into an appropriate expression vector which contains the necessary elements for the transcription of the modified target gene. The expression vector is then transfected into a host cell in order to effectuate expression of the modified target gene in the absence or in the presence of an agent that suppresses the nonsense mutation. In a further embodiment, the expression vector, which contains the necessary elements for the transcription of the modified target gene, is introduced into an individual (without having first been introduced into a host cell that is, in turn, introduced into an individual).

Vectors comprising a modified target gene which contains a nonsense mutation according to the present invention can be manufactured according to methods generally known in the art, for example, by chemical synthesis or recombinant DNA/RNA technology (see, e.g., Sambrook et al., Eds., Molecular Cloning: A Laboratory Manual, 2nd edition, Cold Spring: Harbor University Press, New York (1989); and Ausubel et al., Eds., Current Protocols in Molecular Biology, John Wiley & Sons, New York (1997).

In certain embodiments, the present invention provides a kit for regulating gene expression. The subject kit comprises a vector which comprises: (a) a promoter; (b) an nucleic acid encoding a linker peptide, wherein the nucleic acid is operably linked to the promoter, and wherein the nucleic acid has been modified to contain at least one nonsense mutation located downstream to and in close proximity of the start codon that initiates translation of the linker peptide; and (c) at least one cloning site downstream to the nucleic acid for introducing a target nucleic acid sequence which encodes a target protein to be fused in frame to the carboxyl terminus of the linker peptide. For example, the linker peptide is a signal peptide, which may be a native or a non-native signal peptide of the target protein. Optionally, the kit may further comprise an agent that suppresses a nonsense mutation. To illustrate, such agent is an aminoglycoside antibiotic or an analog thereof (e.g., G418). In certain cases, the agent is an acetylamino benzoic acid compound or a derivative thereof, such as 3-[2-(4-tert-butyl-phenoxyl)-acetylamino]-benzoic acid or 3-{2-[4-(1,1-dimethyl-propyl)-phenoxyl]acetylamino}-benzoic acid.

In certain embodiments, the subject vector or nucleic acid of the present invention comprises a nucleotide element sufficient for initiation of transcription (such as a promoter) operably linked to the nucleic acid encoding the desired target protein. Examples of promoters include, but are not limited to, tRNA promoter, 5S rRNA promoters, histone gene promoters, CMV promoter, RSV promoter, SV40 promoter, PEPCK promoter, MT promoter, SRα promoter, P450 family promoters, GAL7 promoter, $T_7$ promoter, $T_3$ promoter, SP6 promoter, and K11 promoter. The T7 promoter, $T_3$ promoter, SP6 promoter, and $K_{11}$ promoter have been described U.S. Pat. No. 5,591,601, the entire contents of which are incorporated by reference.

In certain embodiments, the invention relates to packaging cell lines useful for generating recombinant viral vectors and viruses comprising a recombinant genome which includes a nucleotide sequence (RNA or DNA) which represents a vector or nucleic acid of the present invention; construction of such cell lines; and methods of using, the recombinant viral vectors to modulate production of a desired target protein in vitro, in vivo and ex vivo. In a particular embodiment, the recombinant viral vectors and viruses comprise a recombinant genome which includes a nucleic acid encoding a target protein, wherein the nucleic acid is operably linked to a promoter and has been modified to contain at least one nonsense mutation downstream to and in close proximity of the start codon that initiates translation of the target protein. Cell lines useful fur generating recombinant viral vectors and viruses are produced by transfecting host cells, such as mammalian host a viral vector including the subject nucleic acid integrated into the genome of the virus, as described herein. Viral stocks are harvested according to methods generally known in the art. See, e.g., Ausubel et al Eds., Current Protocols In Molecular Biology, John Wiley & Sons, New York (1998); Sambrook et al., Eds., Molecular Cloning; A Laboratory Manual, 2nd edition, Cold Spring Harbor University Press, New York (1989); Danos and Mulligan, U.S. Pat. No. 5,449,614; and Mulligan and Wilson, U.S. Pat. No. 5,460,959, the teachings of which are incorporated herein by reference. The recombinant viral vectors produced by the packaging, cell lines of the present invention are also referred to herein as viral vectors which represent the subject nucleic acid.

In certain embodiments, the present invention relates to cells (host cells) which comprise a subject nucleic acid of the invention (e.g., a modified target gene which contains the nonsense mutation). Particular cells which comprise a DNA construct of the invention are discussed above.

In a particular embodiment, a subject nucleic acid construct of the invention can be used to produce transgenic animals whose cells contain and express the nucleic acid construct (e.g., a modified target gene which contains the nonsense mutation). There is a variety of techniques for producing transgenic animals of the present invention. For example, foreign nucleic add can be introduced into the germline of an animal by, for example, introducing the additional foreign genetic material into a gamete, such as an egg. Alternatively, transgenic animals can be produced by breeding animals which transfer the foreign DNA to their progeny. It is also possible to produce transgenic animals by introducing foreign DNA into somatic bells from which an animal is produced. As used herein, the term "transgenic animal" includes animals produced from cells modified to contain foreign DNA or by breeding; that is, it includes the progeny of animals (ancestors) which were produced from such modified cells. As used herein, the term "foreign nucleic acid" refers to a genetic material obtained from a source other than the parental germplasm. Preferably, the transgenic animals are derived from mammalian embryos.

In certain aspects, the invention provides a homologous recombinant non-human animal expressing a subject nucleic acid construct of the invention. The term "homologous recombinant animal" as used herein is intended to describe an animal containing a gene which has been modified by homologous recombination between the gene and a DNA molecule introduced into a cell of the animal, e.g., an embryonic cell of the animal. For example, an animal can be created in which a target gene which has been modified to contain a nonsense mutation is introduced into a specific site of the genome.

In certain cases, to create such a homologous recombinant animal, a vector is prepared which contains a nonsense mutation flanked at its 5' and 3' ends by additional nucleic acid of a eukaryotic gene at which homologous recombination is to occur. The additional nucleic acid flanking the nonsense mutation is of sufficient length for successful homologous recombination with the eukaryotic gene. Typically, several kilobases of flanking DNA (both at the 5' and 3' ends) are included in the vector (see e.g., Thomas, K. R. and Capecchi, M. R. (1987) Cell 51:503 for a description of homologous recombination vectors). The vector is introduced into an embryonic stein cell line (e.g., by electroporation) and cells in which the introduced DNA has homologously recombined with the endogenous DNA are selected (see e.g., Li, E, et al. (1992) Cell 69:915).

In addition to the homologous recombination approaches described above, enzyme-assisted site-specific integration systems are known in the art and can be applied to the components of the regulatory system of the invention to Integrate a DNA molecule at a predetermined location in a second target DNA molecule. Examples of such enzyme-assisted integration systems include the Cre recombinase-lox target system (e.g., as described in Baubonis, W, and Sauer, B. (1993) Nucl. Acids Res. 91:2025-2029; and Fukushige, S. and Sauer, B. (1992) Proc. Natl. Acad. Sci. USA 89; 7905-7909) and the FLP recombinase-FRT target system (e.g., as described in Dang, D. T. and Perrimon, N. (1992) Dev. Genet. 13:367-375; and Fiering, S. et al. (1993) Proc. Natl. Acad. Sci. USA 90:8469-8473).

Methods for acquiring, culturing, maintaining and introducing foreign nucleic acid sequences into recipient eggs for transgenic animal production are well known in the art. See, for example, Manipulating the Mouse Embryo: A Laboratory Manual, Hogan et al., Cold Spring Harbor Laboratory, New York (1986). Preferably, a DNA construct will be delivered into the embryo at a very early stage in development so that only a small frequency of the embryos are mosaic (e.g., an embryo in which integration of the foreign nucleic acid occurs after the one cell stage of development).

Methods of Delivering Nucleic Acids

In certain embodiments, the subject nucleic acid (e.g., a modified target gene which contains the nonsense mutation) can be introduced into a cell by a variety of methods (e.g., transformation, transfection, direct uptake, projectile bombardment, using liposomes). The present invention contemplates any methods generally known in the art which are appropriate for the particular agent or effector and cell type. For example, agents and effectors can be introduced into a cell by direct uptake, DEAE-dextran, calcium phosphate precipitation, lipofection, cell fusion, electroporation, biolistics, microinjection, infection (e.g., by DNA viruses and RNA viruses) and retrovirus-mediated transduction. Such methods are described in more detail, for example, in Sambrook et al., Molecular Cloning: A Laboratory Manual, Second Edition, Cold Spring Harbor University Press, New York (1989); and Ausubel, et al., Current Protocols in Molecular Biology, John Wiley & Sons, New York. (1998). Other suitable methods are also described in the art.

For example, a subject vector of the present invention can also be introduced into a cell by targeting the vector to cell membrane phospholipids. For example, targeting of a vector of the present invention can be accomplished by linking the vector molecule to a VSV-G protein, a viral protein with affinity for all cell membrane phospholipids. Such a construct can be produced using methods well known to those practiced in the art. In those embodiments of the method in which a vector that contains the necessary elements for the transcription of the modified target gene is introduced into an individual, the vector can be introduced by any route which results in delivery to the desired location(s) in the individual. For example, it can be injected (e.g., intramuscularly, intraperitoneally, subcutaneously); introduced intravenously, rectally, orally, or by inhalation; applied topically/administered transdermally or by any other appropriate parenteral or nonparenteral route. In these embodiments, the vector can be present in an appropriate carrier, such as water, physiological buffer, or a lipid based carrier. Other routes of administration and carriers are described herein.

In a particular embodiment, vectors of the invention include, but are not limited to, a DNA plasmid, virus or other suitable replicon (e.g., viral vector). Viral vectors include retrovirus, adenovirus, parvovirus (e.g., adeno-associated viruses), coronavirus, negative strand RNA viruses such as orthomyxovirus (e.g., influenza virus), rhabdovirus (e.g., rabies and vesicular stomatitis virus), paramyxovirus (e.g., measles and Sendai), positive strand RNA viruses such as picornavirus and alphavirus, and double stranded DNA viruses including adenovirus, herpesvirus (e.g., Herpes Simplex virus types 1 and 2, Epstein-Barr virus, cytomegalovirus), and poxvirus (e.g., vaccinia, fowlpox and canarypox). Other viruses include Norwalk virus, togavirus, flavivirus, reoviruses, papovavirus, hepadnavirus, and hepatitis virus, for example. Examples of retroviruses include: avian leukosis-sarcoma, mammalian C-type, B-type viruses, D-type viruses, HTLV-BLV group, lentivirus, spumavirus (Coffin, J. M., Retroviridae: The viruses and their replication, In Fundamental Virology, Third Edition, B. N. Fields, et al., Eds., Lippincott-Raven Publishers, Philadelphia, 1996). Other examples include murine leukemia viruses, murine sarcoma viruses, mouse mammary tumor virus, bovine leukemia virus, feline leukemia virus, feline sarcoma virus, avian leukemia virus, human T-cell leukemia virus, baboon endogenous virus, Gibbon ape leukemia virus, Mason Pfizer monkey virus, simian immunodeficiency virus, simian sarcoma virus, Rous sarcoma virus and lentiviruses. Other examples of vectors are described, for example, in McVey et al., U.S. Pat. No. 5,801,030, the teachings of which are incorporated herein by reference.

Virus stocks consisting of recombinant viral vectors comprising a recombinant genome which includes a nucleic acid of the present invention (e.g., a modified target gene which contains the nonsense mutation), are produced by maintaining the transfected cells under conditions suitable for virus production. Such conditions, which are not critical to the invention, are generally known in the art. See, e.g., Sambrook et al., Molecular Cloning: A Laboratory Manual, Second Edition, Cold Spring Harbor University Press, New York (1989); Ausubel et al., Current Protocols in Molecular Biology, John Wiley & Sons, New York (1998); U.S. Pat. Nos. 5,449,614; and 5,460,959, the teachings of which are incorporated herein by reference. The resulting recombinant viral vectors can be used, as described herein, to modulate production of a desired target protein in vitro, in vivo and ex vivo.

Regulation of Gene Expression

In certain embodiments, the present invention relates to methods of regulating expression of a target protein in vitro, in vivo, and ex vivo, after one or more nonsense mutations have been introduced into a nucleic acid encoding the target protein. Expression of the target protein is regulated by contacting cell with or administering to an animal an agent that suppresses the nonsense mutation, such that expression of the target protein is induced in the cell or animal to a significant level relative to an appropriate control cell or animal. The Examples below describe in detail how to determine a significant level of induction relative to an appropriate control cell or animal.

For example, in certain cases, "a significant level" of induction can be represented by a number of fold of induction by a nonsense mutation suppressor. To illustrate, "a significant lever" of induction may be represented by a 20-, 40-, 60-, 100-, or 200-fold of induction mediated by a nonsense mutation suppressor. In these cases, an "appropriate control" cell or animal refers to a cell or animal in which an agent which suppresses the nonsense mutation is not contacted or administered, while the control cell or animal, like the test cell or animal, comprises a nucleic acid construct (e.g., a nucleic acid which has been modified to contain one or more nonsense mutations).

In other cases, "a significant level" of induction, as used herein, can be represented by a high level of suppression of translation by a nonsense mutation suppressor. In this case, the level of suppression of translation is calculated as a level of the target protein produced by a modified nucleic acid which contains a nonsense mutation, relative to a level of the target protein produced by a wildtype nucleic acid which does not contain the nonsense mutation. To illustrate, "a significant level" of induction is achieved if a target protein is produced from a modified nucleic acid in the presence of a nonsense mutation suppressor at 40%, 50%, 60%, 70%, 80%, 90%, or 100% of the expression level produced from a wildtype nucleic acid. In these cases, an "appropriate control" cell or animal refers to a cell or animal which comprises a wildtype nucleic acid construct (e.g., a nucleic acid does not contain a nonsense mutation).

In one embodiment, an agent that suppresses the nonsense mutation (also referred to as a suppressor or inhibitor of nonsense mutation) is an aminoglycoside. Aminoglycosides are a class of compounds with antibiotic properties. It is known that at least some of their antibiotic effect occurs through a mechanism whereby translation at the ribosomal subunits is disrupted. Aminoglycosides preferentially bind to the 30S eukaryotic ribosomal subunit. At certain subtoxic concentrations, the partial effect of aminoglycosides on the translation machinery is to reduce the fidelity of the translation machinery, such that codons for termination are misread to be codons for amino acids (e.g., tyrosine). Examples of the aminoglycosides include, but are not limited to, hygromycin-B, paromomycin, tobramycin, gentamycin, and G418. As used herein, the term "aminoglycoside" is intended to include pharmaceutically acceptable salts thereof, such as sulfates thereof (e.g., gentamycin sulfate).

In another embodiment, an agent that suppresses the nonsense mutation is an acetylamino benzoic acid compound or a derivative thereof. Examples of the acetylamino benzoic acid compound includes, but are not limited to, 3-[2-(4-tert-butyl-phenoxyl)-acetylamino]-benzoic acid and 3-{2-[4-(1,1-dimethyl-propyl)-phenoxyl]acetylamino}-benzoic acid. Further exemplary acetylamino benzoic acid compounds or derivatives thereof are described in the art (see, e.g., published PCT application WO 2004/009533, the teachings of which are incorporated herein by reference).

In certain embodiments, the present invention relates to regulating expression of a target protein which has therapeutic applications (also referred to as a "therapeutic protein"). Examples of the therapeutic proteins include, but are not limited to, erythropoietin, insulin, vascular endothelial cell growth factors (VEGFs); modified VEGF receptor or fragments thereof, fibroblast growth factors (FGFs), Hypoxia-Inducing Factor-1α (HTF-1α), Factor VIII, Factor IX, Growth Hormone, endostatin, angiostatin and Herpes Simplex Virus Thymidine Kinase.

Screening Methods

In certain embodiments, the present invention relates to methods for screening for suppressors of a nonsense mutation which can induce expression of the target protein in a cell or an animal to a significant level relative to an appropriate control cell or animal. Optionally, such an agent may be able to suppress all three nonsense mutations. Alternatively, such an agent may be able to suppress a specific nonsense mutation, and not other nonsense mutations. A suppressor of a nonsense mutation is utilized in the gene regulation methods of the invention at a concentration that effectively suppresses the nonsense mutation in the target gene, but is not toxic to the host cell.

A variety of assay formats will suffice and, in light of the present disclosure, those not expressly described herein will nevertheless be comprehended by one of ordinary skill in the art. Agents to be tested for their ability to suppress nonsense mutations can be produced, for example, by bacteria, yeast, plants or other organisms (e.g., natural products), produced chemically (e.g., small molecules), or produced recombinantly. Candidate agents contemplated by the present invention include non-peptidyl organic molecules, peptides, polypeptides, peptidomimetics, sugars, hormones, and nucleic acid molecules. In certain embodiments, the candidate agent is an antibiotic. In other embodiments, the candidate agent is an acetylamino benzoic acid compound. In certain further embodiments, the candidate agent is an analogue or derivatives of aminoglycoside antibiotics or acetylamino benzoic acid compounds.

The test agents cart be provided as single, discrete entities, or provided in libraries of greater complexity, such as made by combinatorial chemistry. These libraries can comprise, for example, alcohols, alkyl halides, amities, amides, esters, aldehydes, ethers and other classes of organic compounds. Presentation of test compounds to the test system can be in either an isolated form or as mixtures of compounds, especially in initial screening steps.

In some cases, one or more compounds can be tested simultaneously. Where a mixture of compounds is tested, the compounds selected by the foregoing processes can be separated (as appropriate) and identified by suitable methods (e.g., PCR, sequencing, chromatography). Large combinatorial libraries of compounds (e.g., organic compounds, peptides, nucleic acids) produced by combinatorial chemical synthesis or other methods can be tested (see e.g., Ohlmeyer, M. H. J. et al., Proc. Natl. Aced. Sci. USA 90:10922-10926 (1993) and DeWitt, S. H. et al., Proc. Natl. Acad. Sci. USA 90:6909-6913 (1993), relating to tagged compounds; see also, Rutter, W. J. et al., U.S. Pat. No. 5,010,175; Huebner, V. D. et al., U.S. Pat. No. 5,182,366; and Geysen, H. M., U.S. Pat. No. 4,833,092).

Methods of Treatment and Administration

In certain embodiments, agents and effectors of the present invention, including a subject nucleic acid (e.g., a modified nucleic acid encoding a target protein) and a suppressor of a nonsense mutation, can be introduced into a cell for therapeutic applications. As used herein, a cell includes, but is not limited to, a eukaryotic cell, such as an animal, plant or yeast cell. A cell which is of animal or plant origin can be a stem cell or somatic cell. Suitable animal cells can be of, for example, mammalian or avian origin. Examples of mammalian cells include human (such as HeLa cells), bovine, ovine, porcine, marine, (such as embryonic stem cells), rabbit and monkey (such as COS1 cells) cells. The cell may be an embryonic cell, bone marrow stem cell or other progenitor cell. Where the cell is a somatic cell, the cell can be, for example, an epithelial cell, fibroblast, smooth muscle cell, blood cell (including a hematopoietic cell, red blood cell, T-cell, B-cell, etc.), tumor cell, cardiac muscle cell, macrophage, dendritic cell, neuronal cell (e.g., a glial cell or astrocyte), or pathogen-infected cell (e.g., those infected by bacteria, viruses, virusoids, parasites, or prions).

The cells can be obtained commercially or from a depository or obtained directly from an individual, such as by biopsy. The cells used can be obtained from an individual to whom they will be returned or from another/different individual of the same or different species. For example, nonhuman cells, such as pig cells, can be modified to include a DNA construct and then introduced into a human. Alternatively, the cell need not be isolated from the individual where, for example, it is desirable to deliver the vector to the individual in gene therapy.

For example, the present invention relates to a method of regulating expression of an endogenous gene (a gene resident in a cell as the cell was obtained) to produce a desired target protein and compositions useful in the method. The endogenous gene can be one which is expressed ("on") in the cell or one which is normally not expressed ("off") in the cell but whose expression is or has been turned on or activated. For example, a nucleic acid which has been modified to contain a nonsense mutation, or a virus or viral vector comprising such nucleic acid, can be introduced into genomic DNA of cells. As a result of the introduction of the nonsense mutation, a target protein encoded by the nucleic acid is not produced or produced at a low level in the cells in the absence of a suppressor of the nonsense mutation. In the presence of a suppressor of the nonsense mutation, translation of the target protein is restored, leading to expression of the target protein. In an alternative embodiment, a nucleic acid which has been modified to contain a nonsense mutation, or a virus or viral vector comprising such nucleic acid, is introduced into the endogenous gene encoding the target protein. The resulting cells can be used, as described herein, to regulate production of the target protein in an individual.

The nucleic acids of the present invention can be used in methods of inducing expression of a target protein in an individual (e.g., a human or other mammal or vertebrate). In these methods, a nucleic acid of the present invention can be introduced into cells obtained from the individual. The cells can be migratory, such as a hematopoietic cell, or non-migratory, such as a solid tumor cell or fibroblast. After treatment in this manner, the resulting cells can be administered to (introduced into) the individual according to methods known to those practiced in the art. To induce expression of the target protein, a nonsense mutation suppressor can be administered to the individual according to methods known to those practiced in the art. Such a treating procedure is sometimes referred to as ex vivo treatment. Ex vivo therapy has been described, for example, in Kasid, et al., Proc. Natl. Acad. Sci. USA, 87:473 (1990); Rosenberg et al., N. Engl. J. Med., 323:570 (1990); Williams et al., Nature, 310:476 (1984); Dick et al., Cell, 42:71 (1985); Keller et al., Nature, 318:149 (1985); and Anderson et al., U.S. Pat. No. 5,399,346.

In certain particular embodiments, the nucleic acids or vectors of the present invention can be administered directly to the individual in order to express (induce expression of) a target protein in an individual. The mode of administration is preferably at the location of the target cells. The administration can be nasally or by injection. Other modes of administration (parenteral, mucosal, systemic, implant, intraperitoneal, oral, intradermal, transdermal, intramuscular, intravenous including infusion and/or bolus injection, subcutaneous, topical, epidural, buccal, rectal, vaginal, etc.) are generally known in the art. The nucleic acids can, preferably, be administered in a pharmaceutically acceptable carrier, such as saline, sterile water, Ringer's solution, or isotonic sodium chloride solution. A nonsense mutation suppressor is then administered to the individual, in whom translation of the target protein is restored, resulting in production of the target protein.

In certain specific embodiments, suppressors of a nonsense mutation are aminoglyosides. Aminoglycosides have been used both in vitro and in vivo for antibiotic purposes and, in certain limited situations, to suppress naturally-occurring stop codon mutations. Thus dosages and routes of administration of aminoglycosides that have been used to suppress naturally-occurring stop codon mutations also can be used to suppress the deliberate mutations of the invention. For example, a non-limiting dosage range of aminoglycoside for use with mammalian cells in culture is 0.05 mg/ml to 1 mg/ml, preferably 0.2 mg/ml. Aminoglycosides are commercially available (e.g., from Sigma Chemical Company) and can be added to culture medium in an aqueous solution. For in vivo treatment, pharmacokinetic data generated in the dog (Morris, T. H. (1995) Lab. Animal 29:16-36) can be used to calculate the allometric dose equivalent for other species of subjects (e.g., humans). For example, for mice an effective dosage for gentamycin sulfate has been found to be 17 mg/kg (Barton-Davis, E. R. (1999) J. Clin. Invest, 104:375-381). The aminoglycoside can be delivered by injection in vivo, such as by subcutaneous injection. Sustained treatment with the aminoglycoside may be necessary in vivo to maintain sustained expression of the gene of interest. For example, in one embodiment, the aminoglycoside is administered by subcutaneous injection at 100%, 200% and 400% of the calculated dose equivalents (based on Morris, T. H. supra) once per day for 14 days. In another embodiment, the aminoglycoside is administered using an osmotic pump. The osmotic pump can be implanted under the skin of the subject. In one embodiment, the pump is loaded with appropriate drug concentrations for the subject to receive 50%, 100% or 200% of the calculated dosage for two weeks.

In other specific embodiments, the present invention relates to acetylamino benzoic acid compounds or derivatives thereof as suppressors of a nonsense mutation. Like aminoglycosides, when these suppressors are to be used in vivo in a subject, a particular compound is chosen that is suitable for in vivo use (e.g., a compound in which any potential side effects are not so severe as to preclude use in vivo). Preferred dosage ranges, and potential toxicity, of these suppressor compounds can be determined using in vitro systems (e.g., cultured cells) or animal model systems. Moreover, the dosage of suppressor compounds to be used either in vitro or in vivo may be adjusted over time to thereby adjust the level of expression of the desired gene.

In certain specific embodiments, agents and effectors can be administered to an individual in a variety of ways. The route of administration depends upon the particular agent or effector. Routes of administration are generally known in the art and include oral, intradermal, transdermal (e.g., in slow release polymers), intramuscular, intraperitoneal, intravenous including infusion and/or bolus injection, subcutaneous, topical, epidural, buccal, rectal, vaginal and intranasal routes. Other suitable routes of administration can also be used, for example, to achieve absorption through epithelial or mucocutaneous linings.

The dosage of agent and effector of the present invention administered to an individual, including frequency of administration, will vary depending upon a variety of factors, including mode and route of administration; size, age, sex, health, body weight and diet of the recipient; nature and extent of symptoms of the disease or disorder being treated; kind of concurrent treatment, frequency of treatment, and the effect desired.

Pharmaceutical Compositions

In certain embodiments, the agent and effector of the present disclosure, including a subject nucleic acid (e.g., a modified nucleic acid encoding a target protein) and a nonsense mutation suppressor, collectively referred to herein as therapeutic agents, are formulated with a pharmaceutically acceptable carrier. Such therapeutic agents can be administered alone or as a component of a pharmaceutical formulation (composition). The therapeutic compositions of the invention can be used alone or in admixture, or in chemical combination, with one or more materials, including other recombinant vectors, materials that increase the biological stability of the recombinant vectors, or materials that increase the ability of the therapeutic compositions to specifically penetrate the relevant cell type. The therapeutic compositions of the invention are administered in pharmaceutically acceptable carriers (e.g., physiological saline), which are selected on the basis of the mode and route of administration, and standard pharmaceutical practice. Suitable pharmaceutical carriers, as well as pharmaceutical necessities for use in pharmaceutical formulations, are described in Remington's Pharmaceutical Sciences, a standard reference text in this field.

The therapeutic compositions of the invention are administered in dosages determined to be appropriate by one skilled in the art. An appropriate dosage is one that effects a desired result, e.g., a reduction in a symptom of a disease sought to be treated. It is expected that the dosages will vary, depending upon the pharmacokinetic and pharmacodynamic characteristics of the particular agent, and its mode and route of administration, as well as the age, weight, and health of the recipient; the nature and extent of any relevant disease; the frequency and duration of the treatment; the type of, if any, concurrent therapy; and the desired effect.

Any method that accomplishes in vivo transfer of nucleic acids into eukaryotic cells can be used. For example, expression constructs thereof can be packaged into liposomes, non-viral nucleic acid-based vectors, erythrocyte ghosts, or microspheres (e.g., microparticles; see, e.g. U.S. Pat. Nos. 4,789,734; and 4,925,673; 3,625,214; and Gregoriadis, Drug Carriers in Biology and Medicine, pp. 287-341 (Academic Press, 1979)). Further, delivery of nucleic acid therapeutic agents can be accomplished by direct injection into target tissues, for example, in a calcium phosphate precipitate or coupled with lipids. In certain cases, the nucleic acid therapeutic agents can be modified to increase their ability to penetrate the target tissue by, e.g., coupling them to lipophilic compounds. In addition, nucleic acid therapeutic agents can be targeted to particular cells by coupling them to ligands specific for receptors on the cell surface of a target cell, nucleic acid therapeutic agents can also be targeted to specific cell types by being conjugated to monoclonal antibodies that specifically bind to cell-type-specific receptors.

For topical administration, a therapeutically effective amount of one or more of the therapeutic agents is applied to the desired site on the skin, preferably in combination with a pharmaceutically acceptable carrier, e.g., a spreadable cream, gel, lotion, or ointment, or a liquid such as saline. For use on the skin, the penetration of the nucleic acids into the tissue may be accomplished by a variety of methods known to those of ordinary skill in this field. For example, the expression constructs may be incorporated into a transdermal patch that is applied to the skin. Preferably, the penetration resulting from these methods is enhanced with a chemical transdermal delivery agent such as dimethyl sulfoxide (DMSO) or the nonionic surfactant, n-decylmethyl sulfoxide (NDMS), as described in Choi et al., Pharmaceutical Res., 7(11):1099, 1990. Dosages for a therapeutically effective amount for topical application would be in the range of 100 ng to 10 mg per treated surface area per day.

Exemplification

The invention now being generally described, it will be more readily understood by reference to the following examples, which are included merely for purposes of illustration of certain embodiments and embodiments of the present invention, and are not intended to limit the invention.

Materials And Methods

1) Vectors, Viral Production, and In Vivo Transduction

Replication incompetent lentiviruses used in the gene transfer experiments were created using a five-plasmid transfection procedure. Briefly, 293T cells were transfected using TranIT 293 (Mirus, Madison, Wis.) according to the manufacturer's instructions with a backbone lentiviral vector together with four expression vectors encoding the packaging proteins gagpol, rev, tat and the G-protein of the vesicular stomatitis virus (VSV). The lentiviral backbone used in the experiments was a SIN non-replicative vector derived from the original pHR'CMV-lacZ vector previously described by Naldini et al (8). The gagpol helper plasmid has been codon-optimized for efficient mammalian expression and modified to severely reduce the homology with the gag sequences present in the vector packaging signal. All of the expression helper plasmids contain only the coding sequences, with minimal 5' or 3' untranslated sequences and no introns. In addition, the backbone contains the Woodchuck Hepatitis virus post-transcriptional regulatory element (WPRE) (9) to enhance levels of transcription and gene expression. Viral supernatants were collected starting 24 hr after transfection, for four consecutive collections every twelve hours, pooled and filtered through a 0.45 µm filter. Viral supenantants were then concentrated ~100 fold by ultracentrifugation in a Beckman centrifuge for 1.5 hr at 16,500 rpm. Using this protocol, titers of $\sim 5 \times 10^8$-$1 \times 10^9$/ml were achieved.

For intratracheal infections, nude mice were anaesthesized and then 100 µl of concentrated virus was delivered upon normal inhalation via a blunt-ended 16-gauge needle inserted in such a way to depress the tongue.

2) HSC Purification and Viral Transduction

Purified HSC were obtained by isolating bone marrow SP cells using fluorescence activated cell sorting after Hoechst staining as previously described (10), with some modifications. Briefly, femurs and tibias from mice were homogenized, and the bone marrow cells were filtered through 70 µm nylon mesh and washed in PBS containing 2% FCS and 0.5% Sodium Azide. Cells were then resuspended in HBSS containing 2% FCS, 10 mM Hepes buffer and antibiotics (all from Gibco, Grand Island, N.Y.) and 8.8 µg/ml Hoechst 33342 (Molecular Probes, Eugene, Oreg.) at a cell concentration of $5 \times 10^6$/ml. Following incubation for 90 min at 37° C., cells were washed once and further purified by using a gradient of Ficoll-Paque™ Plus (Amersham Biosciences AB, Uppsala) to remove red blood cells. Purified marrow cells were then sorted using a MoFlo high speed cell sorter (DakoCytomation, Fort Collins, Col.). Except when specified, cells were kept on ice during the entire procedure. Viral transduction of sorted HSC was performed using StemPro SFM-34 medium (Gibco) containing 10 ng/ml SCF, 100 ng/ml TPO, and 5 µg/ml polybrene. All cytokines were purchased from R&D Systems (Minneapolis, Minn.). Transduction was performed in a 20 µl reaction for 2.4 hr at 37° C. in a well of a 96-round bottom well plate. Cells were then resuspended in 100 µl for transplantation.

3) Bone Marrow Transplantation

All mice were purchased from Jackson Laboratories and maintained in a specific pathogen-free animal facility at Harvard Medical School. Ly5.2 recipient mice were lethally irradiated with 2 doses of 7 Gy, 3 hr apart, one day before BMT and maintained under antibiotic-supplemented water for 15 days. Transduced SP cells from Ly5.1 donors were injected retro-orbitally into recipient mice under isofluorane anesthesia. All animal procedures were approved by the Standing Committee on Animals of Harvard Medical School.

4) In vitro Luciferase Assays

FG 293 cells were infected with viral supernatants at a multiplicity of infection (MOI) of 10. After 72 hours, cells were then split into six well plates, exposed to various concentrations of G1418 for 48 hours, and lysed. Protein extracts were then assayed for luciferase expression using the Promega Luciferase Assay System.

5) Non-Invasive Bioluminescent Imaging

Prior to imaging, mice were anaesthesized and injected with 150 μl luciferin (30 mg/ml) (Xenagen, Alameda, Calif.). A series of bioluminescent images were then taken for up to 30 minutes using the Xenogen IVIS imager. Photon output was quantified at the plateau of the time-course using the Living Image software. Induction in fold was calculated based on the photon output in the animals before and after drug treatment.

Results

1) Design Features of Translation-Based Gene Regulation System

The general strategy for controlling gene expression via the modulation of translational termination is shown in FIG. 1A. To achieve the control of expression of a specific transgene, a translational termination ('nonsense') codon is introduced into transgene coding sequences, close to the AUG codon that serves to initiate translation of the complete protein. The modified transgene is then introduced into a standard mammalian expression vector. Upon introduction of the resulting construct into cells, translation of the transgene-encoding mRNA results in production of only a short, non-functional peptide. Addition of small molecules capable of suppressing translational termination to cells harboring the construct results in production of the full-length desired protein.

To prevent the constitutive generation of truncated transgene products of significant length that might engender immune responses in vivo, we chose to position nonsense codon sequences very close to the initiator AUG, such that translation termination would result in the production of a short two to three amino acid peptide, a peptide size insufficient for classic antigen presentation (11). Such a configuration of sequences was modeled after a naturally occurring nonsense mutation in the human Apolipoprotein CII gene (Apo $CII_{Paris2}$) that results in the near complete loss of the corresponding gene product in a patient carrying the mutation (12). The relevant nucleotide sequences of wild-type (WT) and mutant forms of the Apo CII gene are shown in FIG. 1B. Since a number of previous studies had demonstrated that different translational termination codons are recognized at different efficiencies, as reflected by the levels of 'spontaneous' suppression observed in cells, and that nucleotides directly adjacent to translation termination sequences can affect termination efficiencies and the extent of suppression of termination that can be achieved (13-21), we also chose to evaluate several additional configurations of termination codons and adjacent sequences for both their efficiency of translational termination, and their ability to be suppressed by addition of specific compounds (FIG. 1C and FIG. 3).

Based on previous studies that have shown that aminoglycoside antibiotics are capable of suppressing nonsense mutations in mammalian cell lines and in animal models (13, 14, 19, 20, 22-25), and may act similarly in humans (26), a variety of aminoglycoside antibiotics were chosen as potential 'inducers' of gene expression and evaluated for their relative ability to induce transgene expression via suppression of translation termination. G418 (or "Geneticin") (27) was chosen for our initial studies, based on a number of published reports that it was most effective aminoglycoside for suppressing nonsense mutation in mammalian cells (13, 19, 23, 25).

Figure 2B:
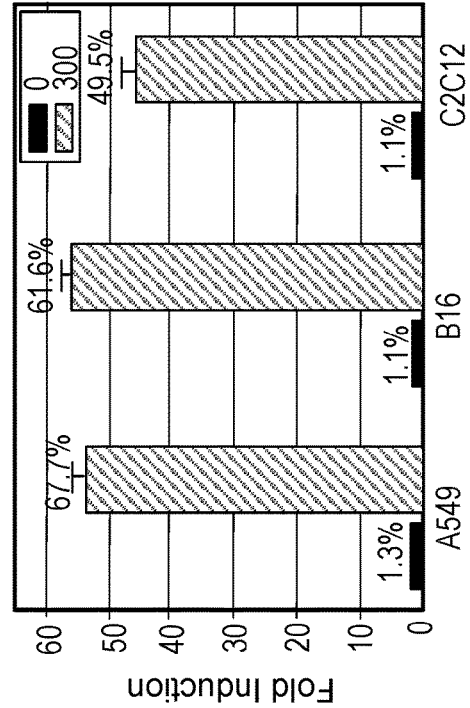
Figure 2D:
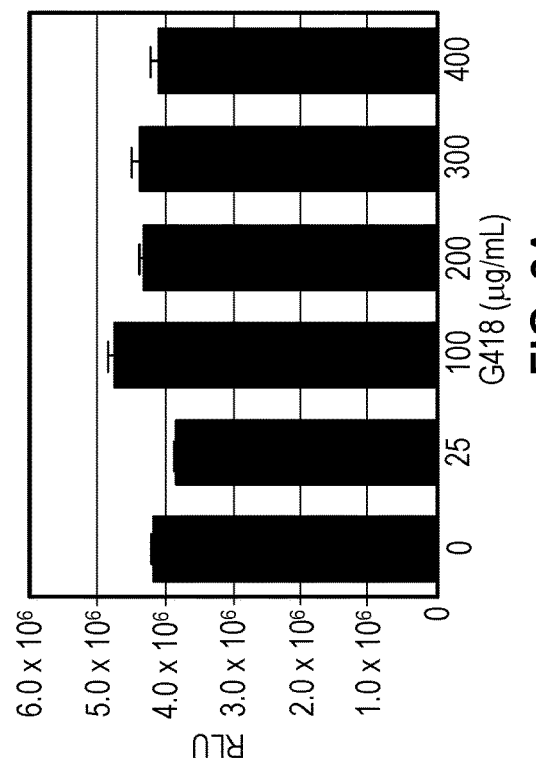
FIG. 2D shows that aminoglycoside-induced suppression of translational termination can be used to regulate gene expression in three other cell types (A549, B16, and C2C12).
Figure 2E:
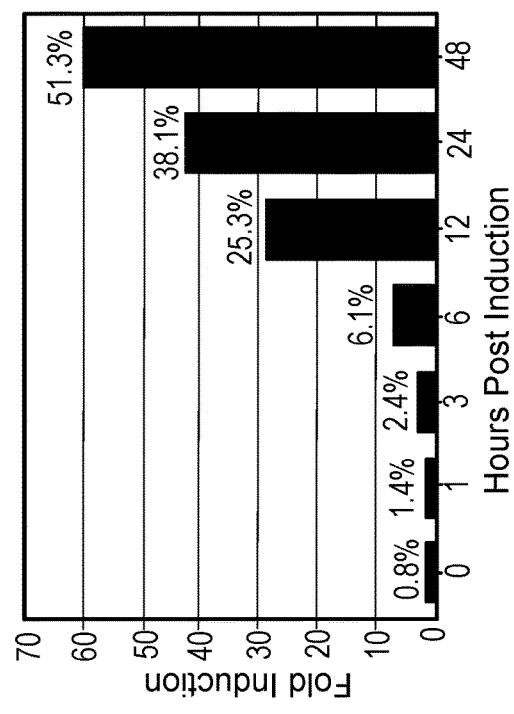
FIG. 2E shows that aminoglycoside-induced suppression of translational termination results in induction of the reporter gene expression (about 60%) as measured by fluorescence-activated cell sorting (FACS) analysis. The red line indicates induced cells, while the blue line indicates uninduced cells.

2) Aminoglycoside-Induced Suppression of a Stop Codon can be Used to Regulate Gene Expression In Vitro To facilitate quantitative measurement of both spontaneous read-through of specific termination codon configurations and the ability of specific antibiotics to suppress translational termination, a luciferase (luc) reporter gene was generated in which the first five codons of either WT mutant MIA-containing) Apo CII sequences were fused to luc coding sequences, and the resulting sequences were introduced into a standard lentiviral vector (FIG. 1B). High-titer virus generated from the vectors was used to infect human FG293 cells at a multiplicity of infection (MOI) of 10, so that virtually 100% of the cells would be stably transduced. Cells were then split into six well plates, exposed to varying concentrations of the aminoglycoside (G418) for 48 hours, and then lysed and assayed for luc expression. As shown in FIG. 2A, cells transduced by vectors encoding wild type Apo CII sequences expressed high levels of luciferase that were not dependent upon the presence of antibiotic. In contrast, cells transduced by vectors encoding the mutant Apo CII-luc expressed only low levels of luc in the absence of G418 (approximately 1.2% the activity of the wild type), but could be induced to strongly express luc by the addition of the antibiotic (FIG. 2B). Maximum induction of expression was observed in the presence of 300 μg/ml of G418, representing an approximately 60-fold increase in reporter expression relative to the induced state. The efficiency of suppression of translational termination was extremely high (over 70% of the level of wild-type reporter expression observed in the absence of the nonsense codon). Northern analysis of RNA isolated from cells transduced with viruses encoding either WT or mutant Apo CII-luciferase fusion proteins showed that comparable amounts of mRNA were produced, whether or not G418 was present (data not shown). This latter data indicates that the configuration of initiator and termination codon used for gene regulation does not appreciably activate the nonsense-mediated mRNA decay (NMD) pathway (28). G418 (or "Geneticin") (27) was chosen for our initial studies, based on a number of published reports that it was most effective aminoglycoside for suppressing nonsense mutation in mammalian cells (13, 19, 23, 25).

2) Aminoglycoside-Induced Suppression of a Stop Codon Can Be Used to Regulate Gene Expression In Vitro To facilitate quantitative measurement of both spontaneous read-through of specific termination codon configurations and the ability of specific antibiotics to suppress translational termination, a luciferase (luc) reporter gene was generated in which the first five codons of either WT mutant (TGA-containing) Apo CII sequences were fused to luc coding sequences, and the resulting sequences were introduced into a standard lentiviral vector (FIG. 1B). High-titer virus generated from the vectors was used to infect human FG293 cells at a multiplicity of infection (MOI) of 10, so that virtually 100% of the cells would be stably transduced. Cells were then split into six well plates, exposed to varying concentrations of the aminoglycoside (G418) for 48 hours, and then lysed and assayed for luc expression. As shown in FIG. 2A, cells transduced by vectors encoding wild type Apo CII sequences expressed high levels of luciferase that were not dependent upon the presence of antibiotic. In contrast, cells transduced by vectors encoding the mutant Apo CII-luc expressed only low levels of luc in the absence of G418 (approximately 1.2% the activity of the wild type), but could be induced to strongly express luc by the addition of the antibiotic (FIG. 2B). Maximum induction of expression was observed in the presence of 300 µg/ml of G418, representing an approximately 60-fold increase in reporter expression relative to the uninduced state. The efficiency of suppression of translational termination was extremely high (over 70% of the level of wild-type reporter expression observed in the absence of the nonsense codon). Northern analysis of RNA isolated from cells transduced with viruses encoding either WT or mutant Apo CII-luciferase fusion proteins showed that comparable amounts of mRNA were produced, whether or not G418 was present (data not shown). This latter data indicates that the configuration of initiator and termination codon used for gene regulation does not appreciably activate the non-sense-mediated mRNA decay (NMD) pathway (28).

Figure 2C:
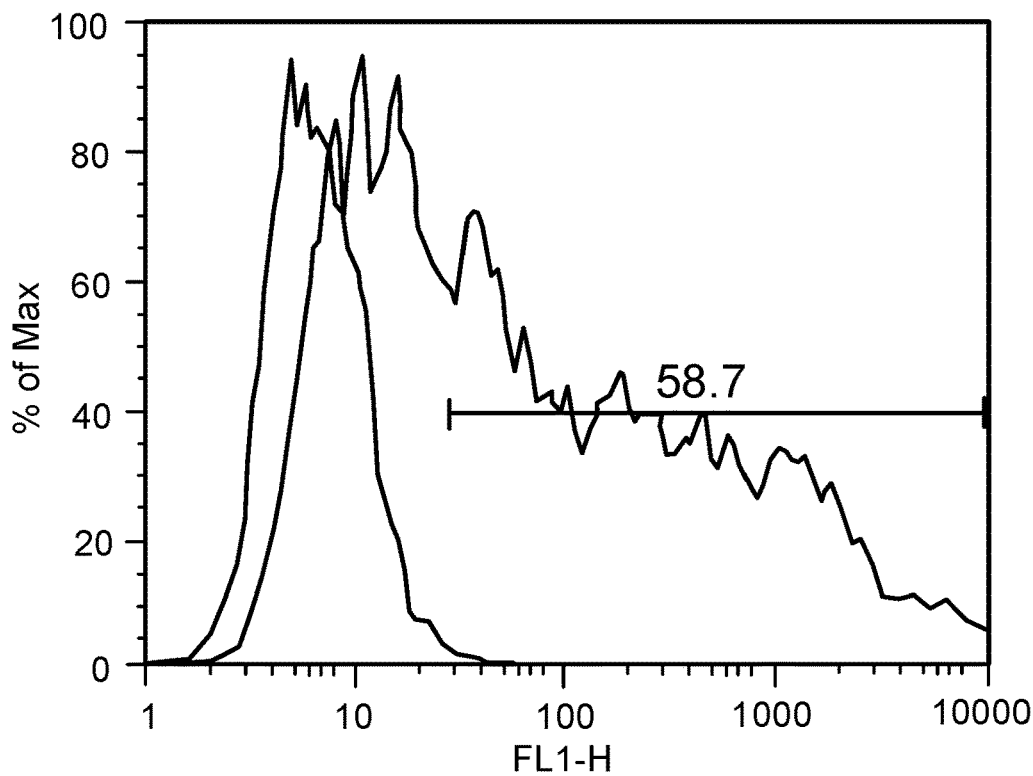

3) Kinetics of Induction of Gene Expression Using Aminoglycoside-Mediated Suppression of Translational Termination One of the expected characteristics of the gene regulation system described here is the ability to rapidly achieve induction of transgene expression, since (as indicated above) transcription is constitutive and therefore induction of gene expression should depend only upon the restoration of fall translation of the transgene coding sequences. To address this issue, we employed the transduced cells described above, and measured the level of reporter activity after G418 administration (200 µg/ml) as a function of time. As shown in FIG. 2C, as soon as 1 hour post induction, the first time period tested, levels of luciferase significantly above the levels observed before addition of drug were detected (1.4% at t=1 hour vs 0.8% wild-type activity at t=0). At 6, 12, and 24 hours post induction, 6.1%, 25.3% and 38.1%, respectively, of wild-type activity was achieved, with maximal induction noted at 48 hours post exposure of the cells to G418 (60-fold induction; 51.3% of wild-type activity).

4) Basal and Inducible Levels of Transgene Expression are Dependent Upon the Choice of Termination Codon and Adjacent Sequences While our initial experiment made use of the precise amino acid sequences represented by mutant human Apo CII $NH_2$-terminal sequences, we next asked whether either the basal or induced levels of transgene expression could be manipulated through the use of other termination codons and surrounding sequences. As shown in FIG. 1C, of all the configurations tested, sequences derived from the Apo $CII_{Paris2}$ (TGAC) gene exhibited the greatest spontaneous read-through (1.2%), and the largest extent of 'induction' with aminoglycoside treatment (61-fold induction, with 73% of WT expression achieved). Interestingly, however, while as expected 19), the ATAAA configuration displayed a significantly lower level of spontaneous read through (0.24%), the levels of induction that could be achieved (42-fold) were quite comparable to those achieved with the TGAC configuration. While the placement of two UGA codons directly adjacent to each other decreased the basal levels of expression (0.39-0.43% of WT expression), the level of induction achieved was only moderate (26 to 28 fold). Introduction of sequences between the two UGA codons to provide a +4 nucleotide previously shown to be permissive to read-through (17) actually led to a further decrease in basal levels (0.11%), and an 18-fold induction. Lastly, the juxtaposition of two UAA codons led to a low basal level (0.22%) but a poor level of induction (5-fold). These studies indicate that specific configurations of termination codons and adjacent nucleotide sequences can indeed be used to provide for different levels of basal and induced gene expression. It should be noted from the sequences shown in FIG. 1C that fortuitously, the mutant Apo CII-derived sequences actually encode an additional AUG directly overlapping the UGA codon. If translated, a peptide of four amino acids might be produced in addition to the expected three amino acid peptide. No fortuitous short open-reading frame is generated as a consequence of utilizing the TAA-containing configurations.

5) G418 is the Most Effective Aminoglycoside Inducer of Gene Expression

Figure 3A:
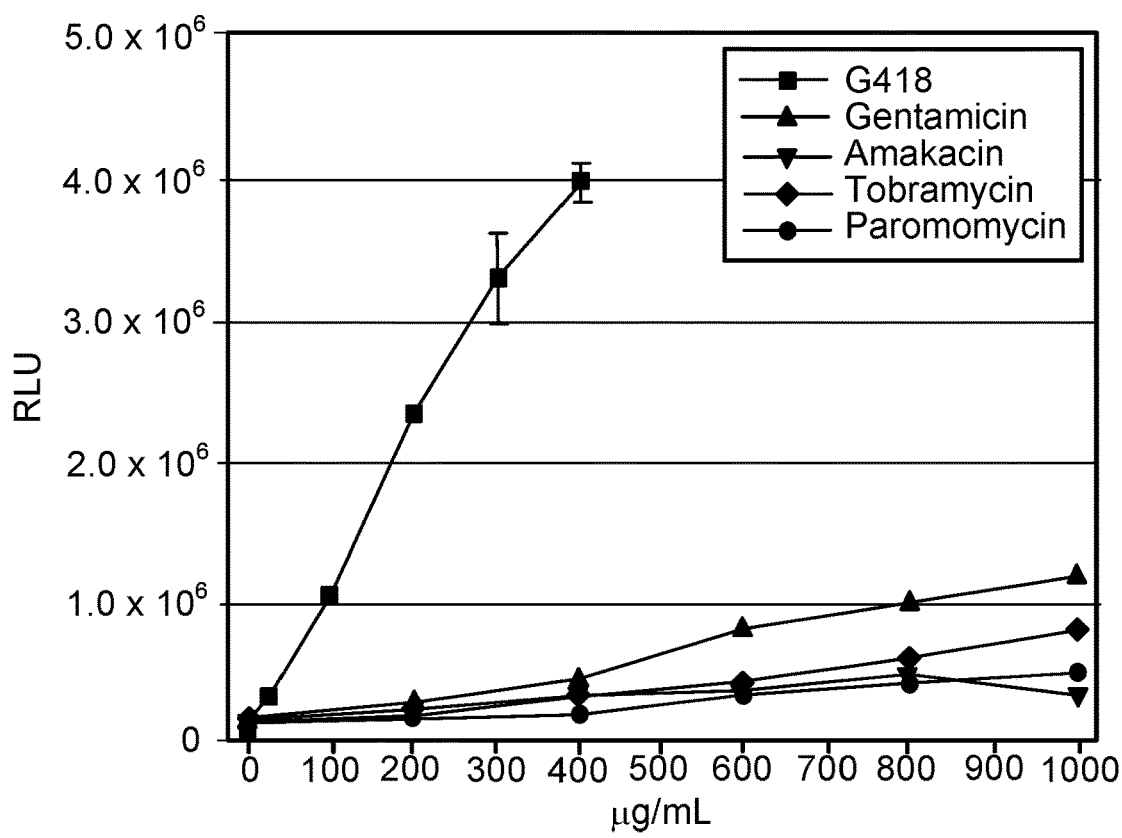
FIG. 3A shows data demonstrating that Geneticin (G418) is the most effective suppressor of translation termination codons. Compounds were tested in vitro using FG293 cells infected with virus encoding the mutant luc fusion product. Amount of expression achieved is expressed in relative light units (RLU). Cells were exposed to drugs at the indicated concentrations for 48 hours prior to being assayed for luc expression, and the results represent the average of three independent experiments.

While several previous studies had strongly suggested that G418 was more effective at suppressing nonsense mutations than other aminoglycosides 23, 25), we sought to confirm this result in the context of the luciferase-based gene regulation assay described above. Compounds were tested in vitro using stable cell lines generated via the infection of FG293 cells with lentiviral vectors carrying either WT or mutant Apo CII luc sequences. The aminoglycosides were tested over a concentration range from 0 to 1000 µg/ml. As shown in FIG. 3A, none of the other aminoglycosides tested (gentamicin, amakacin, tobramycin, and paromomycin) were comparable to G418 in their ability to induce luciferase expression, as they displayed only weak induction throughout the aminoglycoside concentration range tested.

Figure 3B:
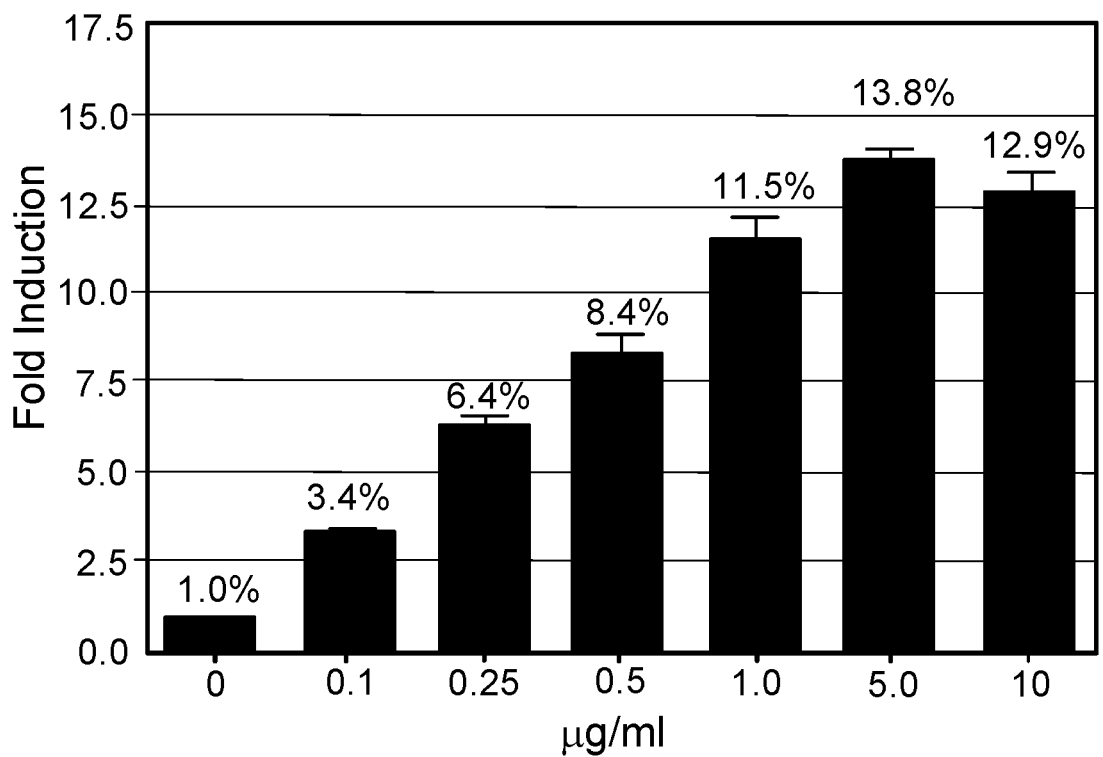
FIGS. 3B and 3C show that two novel compounds are effective in suppressing translation termination codons in FG293 cells.
Figure 3C:
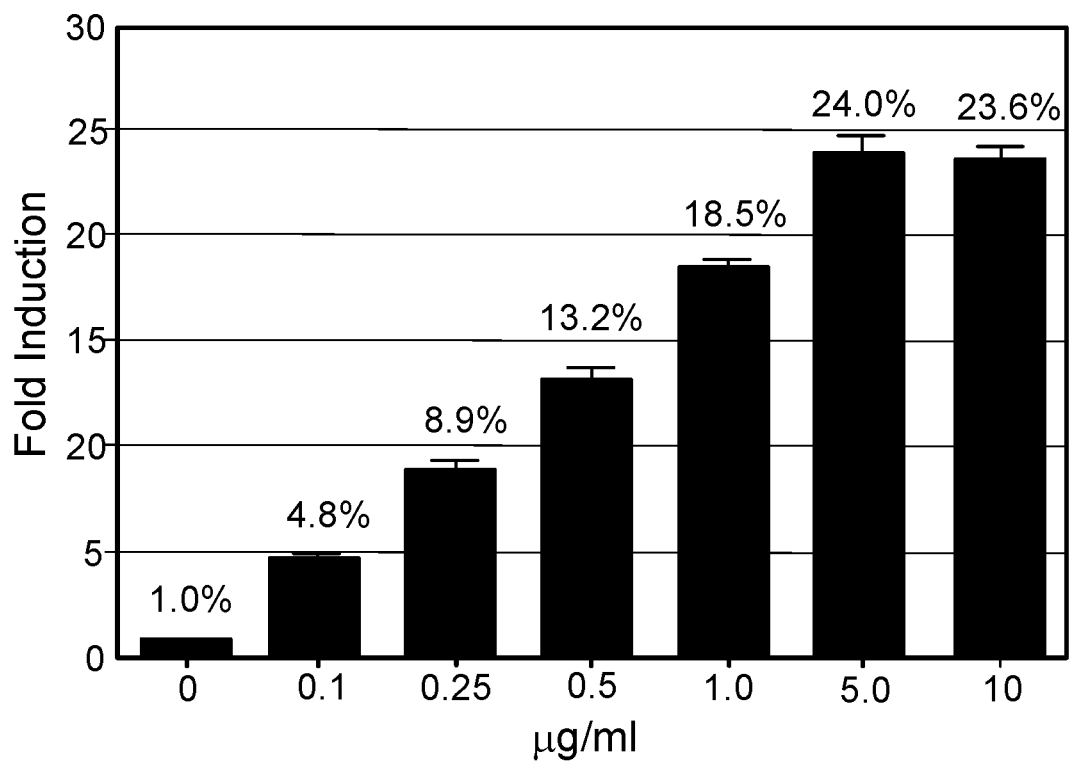

Further, two novel compounds were found to be effective in suppressing translation termination codons FG293 cells. FIG. 3B indicates that the fold of induction mediated by 3-[2-(4-tert-butyl-phenoxyl)-acetylamino]-benzoic acid was about 14% at the concentration of 5 µg/ml. FIG. 3C indicates the fold of induction mediated by 3-{2-[4-(1,1-dimethyl-propyl)-phenoxyl]acetylamino}-benzoic acid was about 24% at the concentration of 5 µg/ml. Both compounds were purchased from Chembridge.

6) Aminoglycoside Induced Suppression of Translational Termination can Regulate Gene Expression In Vivo To further establish the general applicability of the gene retaliation system, we next asked whether gene regulation at the level of translation could be readily accomplished in the in vivo setting. In a first animal model, intratracheal delivery (see Materials and Methods) of a lentiviral vector carrying WT or mutant Apo CII-luc sequences was utilized in order to assess the ability to regulate luc expression in murine lung tissue via aminoglycoside administration. Five days post transduction, prior to administration of aminoglycoside, mice were imaged for luc expression using the Xenogen IVIS non-invasive bioluminescent imager (29). In contrast to the animals infected with the vector encoding WT Apo CII luc Sequences (WT luc mice), which displayed a strong photon signal indicative of luciferase activity, animals that were infected with the vector encoding mutant Apo CII-luc sequences (mutant luc mice) showed no detectable signal (data not shown). Mice were then injected for 4 days, once daily, with either G418 or PBS, except that on the fourth day when mice were injected twice, once in the morning and then again 60 minutes before luciferase imaging. The daily dose of G418 chosen for administration was 1.5 mg, an amount which represents approximately half of the published $LD_{50}$ for G418 (25). As expected, upon imaging, WT luc mice showed strong luc expression, whether or not G418 had been administered. In contrast, while mutant luc mice that were injected with PBS continued to display no detectable luciferase activity, mutant luc mice that were subsequently administered G418 showed significant induction of luciferase activity. The five mice treated in this way displayed significant luciferase expression, resulting in an average of 27% of the level of expression observed in WT luc mice. Due to the lack of detectable luc expression in uninduced mice, it was not possible to determine a 'fold-induction'.

To further evaluate the potential in vivo utility of the gene regulation system, a standard murine bone marrow transplantation model was used to assess the ability to regulate genes introduced into hematopoietic cells via lentiviral vectors. For these studies, 500 purified C57/B16 hematopoietic stem cells (SP cells) (10) were transduced with lentiviral vectors encoding either wild-type or mutant reporters and then introduced into lethally-irradiated recipients. Four weeks after bone marrow transplantation, reconstituted animals were imaged for luciferase expression and then subsequently treated with PBS or G418 daily for 3.5 days (1.5 mg/day). Prior to PBS or G418 administration, animals reconstituted with cells transduced by virus encoding mutant Apo CII luc sequences (mutant luc mice) showed negligible luc expression, while animals reconstituted with cells transduced by viruses encoding WT Apo CII luc sequences (WT luc mice) showed robust luc expression (data not shown). After PBS or G418 administration, WT luc mice continued to show strong luc expression. While PBS administration had no effect on luc expression in mutant luc mice, antibiotic treatment of those mice led to the strong induction of luc. Quantitation of luciferase activity in four mutant luc animals before and after drug administration demonstrated an average 65-fold induction of luc expression, with induced levels approaching an average of 51% of the expression observed in WT luc mice.

7) Aminoglycoside Induced Suppression of Translational Termination Can Effectively Regulate Gene Expression and Secretion of Human Growth Hormone (hGH).

Figure 4:
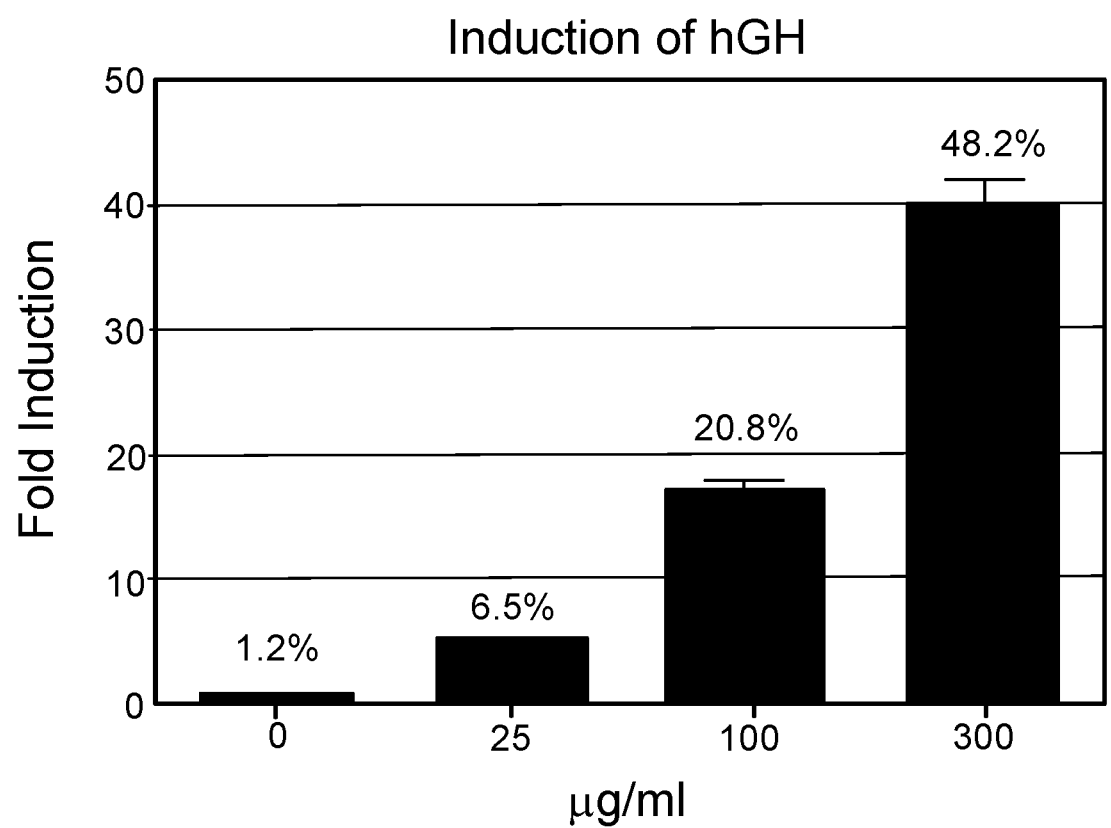
FIG. 4 shows that G418 effectively induces gene expression of human growth hormone gene (hGH) by suppressing translation termination codons, resulting in increased secretion of hGH protein as measured by ELISA.

FIG. 4 presents data that shows that G418 effectively induces gene expression of human growth hormone gene (hGH) by suppressing translation termination codons, resulting in increased secretion of hGH protein as measured by ELISA.

Discussion

The studies reported here demonstrate the feasibility of utilizing translation-based systems for the control of gene expression in mammalian cells both in vitro and in vivo. Perhaps the most important design feature of this gene regulation strategy is its remarkable simplicity: the only 'genetic element' required is an approximately three to ten nucleotide DNA sequence encoding a translational termination codon and in some cases, additional sequences. Because the regulatory element resides within transgene coding sequences, it should be possible to achieve regulation in the context of virtually any expression vector, and to provide for the regulation of expression of protein coding sequences with the context of their normal endogenous control elements. In addition, since we have shown that, at least in the case of the configuration of initiation and termination codons tested, the production of mRNA is constitutive; induction of gene expression should be dependent only on the restoration of translation of the complete coding sequences. Therefore, the kinetics of induction of gene expression would be expected to be more rapid than gene regulation systems based on the control of transcription or mRNA cleavage, in which cases RNA half-life is a relevant variable.

The conception and design of the translation-based gene regulation system described above was strongly guided by a large number of previous studies which have focused on the phenomenon of translational 'miscoding' in mammalian cells (30). Those studies have provided a detailed understanding of both the local sequence contexts that affect the extent of spontaneous read-through of different termination codons, and the ability or specific aminoglycoside antibiotics to enhance such read-through (13-21). The known sequence determinants governing the efficiency of the spontaneous read-through of termination codons were particularly germaine to our studies, in so far as they enabled the design of regulatory elements that provided for different levels of 'basal' and 'induced' gene expression, an important practical capability of the strategy. While our studies explored only a small number of permutations of sequences encoding different termination codons and adjacent sequences, the available literature suggests that parameters of regulation such as basal and induced levels of expression could be very precisely manipulated by the empirical evaluation of a wide range of different sequence configurations.

In the case of the present studies, the positioning of the nonsense codon relative to transgene coding sequences was based upon the existence of a naturally occurring mutation in the human Apo CII gene (Apo $CII_{Paris2}$) known to dramatically affect production of the normal gene product in a patient carrying the mutation (12). The close juxtaposition of initiation and termination codons, represented by the Apo CII mutation, was thought to an important design feature of the translation-based regulation system, since the small peptide resulting from the premature termination of translation initiating from the authentic AUG would be too small to enter the classic pathway for antigen presentation (11). Clearly, however, as was pointed out earlier with regard to the Apo CII sequences used in our studies, depending upon the specific coding sequences of the transgene, there may be the possibility of producing other truncated peptides. In such cases, additional modifications of sequences may be warranted.

Another benefit of the placement of the termination codon close to the beginning of protein-coding sequences shown by our studies is that this specific configuration did not lead to any appreciatiable reduction of mRNA levels due to activation of the NMD pathway (28), a response that might compromise either the extent or kinetics of 'induction' of gene expression. Our data is consistent with a very recent study which showed that a naturally occurring mRNA which possessed a nonsense mutation located close to the initiator AUG was not subject to nonsense-mediated mRNA decay (NMD) (31).

Lastly, with regard to the placement of nonsense codons adjacent to the initiator AUG, it is noteworthy that in the case of several configurations of sequences we evaluated, it was possible to obtain extremely high levels of suppression of translation by aminoglycoside administration, in some cases over 70% the levels of wild-type gene expression. As such high levels of suppression have not been previously reported by others, it is possible that the placement of termination codons close to the initiator codon may uniquely facilitate the suppression of translational termination by aminoglycosides. Future experiments will address this issue as well as the role, if any, of the strength of the termination codon at the end of transgene protein coding sequences in determining suppression efficiencies.

One limitation of the design of the system is that introduction of the 'regulatory element' into transgene sequences can alter the amino acid sequence of the resulting gene product. While for many experimental applications, slight alterations in amino acid sequences may be irrelevant, in certain cases, regulation of an authentic gene product may be critical. This limitation may be addressed in several ways. First, depending on the native amino acid sequence of the protein of interest, it may be possible to design configurations in which substitution of a single amino acid codon with a specific termination codon is sufficient for gene regulation, taking account of knowledge regarding the specific amino acids that are inserted when specific nonsense codons are misread (32) and the effects of nucleotides directly adjacent to termination codons on the efficiency of termination (17, 19). In this regard, we have shown that it was possible to achieve efficient gene regulation of a gene product through substitution of only two amino acid codons present in a coding sequence (unpublished results). In that particular case, the termination codon fortuitously replaced an amino acid codon specifying the same amino acid as that which would be predicted to be introduced by misreading of the termination codon (32). Second, in the special case of regulating the expression of secreted gene products, in which the mature gene product is generated by co-translational cleavage of the pre-protein (33), modifications of sequences adjacent to the initiator AUG should not affect the structure of the mature gene product and therefore it should generally be possible to regulate expression of an authentic secreted product. In recent studies, we have documented the ability to provide for the regulated expression of a secreted gene product, through the introduction of a nonsense codon into 'signal peptide' encoding sequences (unpublished results).

Overall, the system described here represents a remarkably simple means of controlling the expression of genes in mammalian cells that should have immediate experimental applications. While the range of inducibility obtainable with the system (in some cases over 60 fold) is considerably more limited than that of gene regulation systems based on the control of transcription or RNA self-cleavage, the ability to fine-tune the basal and induced levels of gene expression via use of specific termination codons and adjacent sequences may mitigate this limitation in many experimental situations. With regard to the issue of the availability of suitable inducers for common experimental applications, it is ironic that we and other have shown that the most effective aminoglycoside for suppressing nonsense mutations in mammalian cells is G418 (Geneticin), an antibiotic most well known to molecular biologists for its ability to cells in the context of selections for transduced cells (34). Despite this 'reputation', we have shown here that G418 can be effectively utilized to regulate gene expression in a number of cell lines and in animals at concentrations that are not acutely toxic. Similarly, others have shown that G418 can be used at relatively non-toxic doses to suppress nonsense mutations in cell lines and in animal models of inherited disease (25, 35). These results may lend support to the notion that the requirements for the suppression of normal translational termination at the end of protein coding sequences may be more stringent than those important for the suppression of nonsense mutations. Furthermore, based on a number of animal studies that suggest the possibility that the suppression of nonsense mutations could provide a novel therapeutic approach to the treatment of certain inherited diseases (19, 22-25, 36), there have been intense efforts to identify non-toxic small molecules suitable for use in humans. The availability of such molecules for experimental studies in the future should further expand the utility of translation-based gene regulation strategies.

REFERENCES

1. Gossen, M, & Bujard, H. (1992) *Proc Natl Acad Sci USA* 89, 5547-51.
2. Wang, Y., O'Malley, B. W., Jr., Tsai, S. Y. & O'Malley B. W, (1994) *Proc Natl Acad Sci USA* 91, 8180-4.
3. Rivera, V. M., Clackson, T., Natesan, S., Pollock, R., Amara, J. F., Keenan, T., Magari, S. R., Phillips, T., Courage, N. L., Cerasoli, F., Jr., Holt, D. A. & Gilman, M. (1996) *Nat Med* 2, 1028-32.
4. Suhr, S. T., Gil, E. B., Senut, M. C. & Gage, F. H. (1998) *Proc Natl Acad Sci USA* 95, 7999-8004.
5. Gossen, M., Bonin, A. L., Freundlieb, S. & Bujard, H. (1994) *Curr Opin Biotechnol* 5, 516-20.
6. Rivera, V. M., Gao, G. P., Grant, R. L., Schnell, M. A., Zoltick, P. W., Rozamus, L. W., Clackson, T. & Wilson J. M. (2005) *Blood* 105, 1424-30.
7. Yen, L., Svendsen, J., Lee, J. S., Gray, J. T., Magnier, M., Baba, T., D'Amato, R. J. & Mulligan, R. C. (2004) *Nature* 431, 471-6.
8. Naldini, L., Blomer, U., Gallay, P., Ory, D., Mulligan, R., Gage, F. H., Verma, I. M. & Trono, D., (1996) *Science* 272, 263-7.
9. Zufferey, R., Donello, J. E., Trono, D. & Hope, T. J. (1999) *J. Virol* 73, 2886-92.
10. Goodell, M. A., Brose, K., Paradis, G., Conner, A. S. & Mulligan, R. C. (1996) *J Exp Med* 183, 1797-806.
11. Rammensee, H. G., Falk, K. & Rotzschke, O., (1993) *Annu Rev Immunol* 11, 213-44.
12. Parrott, C. L., Alsayed, N., Rebourcet, R. & Santamarina-Fojo, S. (1992) *J Lipid Res* 33, 361-7.
13. Burke, J. F. & Mogg, A. E. (1985) *Nucleic Acids Res* 13, 6265-72.
14. Martin, R., Mogg, A. E., Heywood, L. A., Nitschke, L. & Burke, J. F. (1989) *Mol Gen Genet* 217, 411-8.
15. Brown, C. M., Stockwell, P. A., Trotman, C. N. & Tate, W. P. (1990) *Nucleic Acids Res* 18, 6339-45.
16. Martin, R. (1994) *Nucleic Acids Res* 22, 15-9.
17. McCaughan, K. K., Brown, C. M., Dalphin, M. E., Berry, M. J. & Tate, W. P. (1995) *Proc Natl Acad. Sci USA* 92, 5431-5.
18. Phillips-Jones, M. K., Hill, L. S., Atkinson, J. & Martin, R. (1995) *Mol Cell Biol* 15, 6593-600.
19. Howard, M. T., Shirts, B. H., Petros, L. M., Flanigan, K. M., Gesteland, R. F. & Atkins, J. F. (2000) *Ann Neurol* 48, 164-9.
20. Manuvakhova, M., Keeling, K. & Bedwell, D. M. (2000) *Rna* 6, 1044-55.
21. Namy, O., Hatin, I. & Rousset, J. P. (2001) *EMBO Rep* 2, 787-93.
22. Barton-Davis, E. R., Cordier, L., Shoturma, D. L., Leland, S. E. & Sweeney, H. L. (1999) *J. Clin Invest* 184, 375-81.
23. Howard, M. T., Anderson, C. B., Fass, U., Khatari, S., Gesteland, R. F., Atkins, J. F. & Flanigan, K. M. (2004) *Ann Neurol* 55, 422-6.
24. Hein, L. K., Bawden, M., Muller, V. J., Sillence, D., Hopwood, J. J. & Brooks, D. A. (2004) *J Mol Biol* 338, 453-62.
25. Sankuhl, K. Schulz, A. Rompler, H., Yun, J., Wess, J. & Schoneberg, T. (2004) *Hum Mol Genet* 13, 893-903.
26. Wilschanski, M., Yahav, Y., Yaacov, Y., Blau, H., Bentur, L., Rivlin, J., Aviram, M., Bdolah-Abram, T., Bebok, Z., Shushi, L., Kerem, B. & Kerem, E. (2003) *N Engl J. Med* 349, 1433-41.
27. Loebenberg, D., Counels, M. & Waitz, J. A. (1975) *Antimicrob Agents Chemother* 7, 811-5.

28. Frischmeyer, P. A. & Dietz, H. C. (1999) *Hum Mol Genet* 8, 1893-900.
29. Contag, C. H. & Bachmann, M. H. (2002) *Annu Rev Biomed Eng* 4, 235-60.
30. Gesteland, R. F. Weiss, R. B. & Atkins, J. F. (1992) *Science* 257, 1640-1.
31. Inacio, A., Silva, A. L., Pinto, J., Ji, X., Morgado, A., Almeida, F., Faustino, P., Lavinha, J., Liebhaber, S. A. & Romao, L. (2004) *J Biol Chem* 279, 32170-80.
32. Nilsson, M. & Ryden-Aulin, M. (2003) *Biochim Biophys Acta* 1627, 1-6.
33. Rothman, J. E. (1994) *Nature* 372, 55-63.
34. Colbere-Garapin, F., Horodniceanu, F., Kourilsky, P. & Garapin, A. C. (1981) *J Mol Biol* 150, 1-14.
35. Lai, C. H., Chun, H. H., Nahas, S. A., Mitui, M., Gamo, K. M., Du, L. & Gatti R. A. (2004) *Proc Natl Acad Sci USA* 101, 15676-81.
36. Howard, M., Frizzell, R. A. & Bedwell, D. M. (1996) *Nat Med* 2, 467-9.

INCORPORATION BY REFERENCE

All publications and patents mentioned herein are hereby incorporated by reference in their entirety as if each individual publication or patent was specifically and individually indicated to be incorporated by reference.

While specific embodiments of the subject invention have been discussed, the above specification is illustrative and not restrictive. Many variations of the invention will become apparent to those skilled in the art upon review of this specification and the claims below. The scope of the invention should be determined by reference to the claims, along with their full scope of equivalents, and the specification, along with such variations.

---

We claim:

1. A recombinant polynucleotide molecule comprising a nucleic acid encoding a target protein, wherein the nucleic acid is operably linked to a promoter and has been modified to contain a nonsense codon, wherein the nonsense codon is a codon TGA present as TGAC in the nucleotide sequence, and wherein the number of codons between the start codon that initiates translation of the target protein and the nonsense codon is 2.

2. The polynucleotide molecule of claim 1, wherein the target protein comprises a signal peptide.

3. The polynucleotide molecule of claim 2, wherein the target protein is a secreted protein.

4. The polynucleotide molecule of claim 3, wherein the nonsense codon is introduced in a region of the nucleic acid which encodes the signal peptide.

5. An isolated cell comprising a genome comprising the polynucleotide molecule of claim 1.

6. A vector comprising the polynucleotide molecule of claim 1.

7. The vector of claim 6, wherein the vector is a viral vector.

8. An isolated cell comprising the polynucleotide molecule of claim 1.

9. The isolated cell of claim 5, wherein the isolated cell is a mammalian cell.

10. The isolated cell of claim 8, wherein the isolated cell is a mammalian cell and further comprises an agent which suppresses the nonsense codon.

11. A recombinant vector for inducible expression of a target protein comprising:
   a) a promoter;
   b) a nucleic acid comprising a start codon and encoding a linker peptide, wherein the nucleic acid is operably linked to the promoter and has been modified to contain a nonsense codon; and
   c) at least one cloning site downstream to the nucleic acid for introducing a target nucleic acid sequence which encodes the target protein to be fused in frame to the carboxyl terminus of the linker peptide,
   wherein the nonsense codon is a codon TGA present as TGAC in the nucleotide sequence, and wherein the number of codons between the start codon and the nonsense codon is 2.

12. The vector of claim 11, wherein the linker peptide is a signal peptide.

13. The vector of claim 12, wherein the signal peptide is a native or a non-native signal peptide of the target protein.

* * * * *

UNITED STATES PATENT AND TRADEMARK OFFICE
CERTIFICATE OF CORRECTION

PATENT NO. : 11,517,630 B2
APPLICATION NO. : 16/200974
DATED : December 6, 2022
INVENTOR(S) : Richard Mulligan and George J. Murphy It is certified that error appears in the above-identified patent and that said Letters Patent is hereby corrected as shown below:

In the Specification

Column 1, Line 15, delete "NIH 5PO-HL54785" and insert -- HL054785, --;

Column 1, Line 15, after "by" insert -- the --;

Column 1, Line 16, delete "government" and insert -- Government --.

Signed and Sealed this
Twenty-eighth Day of November, 2023

Katherine Kelly Vidal
*Director of the United States Patent and Trademark Office*

SEQUENCE LISTING

<160> NUMBER OF SEQ ID NOS: 10

<210> SEQ ID NO 1
<211> LENGTH: 15
<212> TYPE: DNA
<213> ORGANISM: Artificial Sequence
<220> FEATURE:
<223> OTHER INFORMATION: modified human nucleic acid

<400> SEQUENCE: 1
atgggcacat aactc                                                15

<210> SEQ ID NO 2
<211> LENGTH: 15
<212> TYPE: DNA
<213> ORGANISM: Artificial Sequence
<220> FEATURE:
<223> OTHER INFORMATION: modified human nucleic acid

<400> SEQUENCE: 2
atgggcacat gactc                                                15

<210> SEQ ID NO 3
<211> LENGTH: 15
<212> TYPE: DNA
<213> ORGANISM: Artificial Sequence
<220> FEATURE:
<223> OTHER INFORMATION: modified human nucleic acid

<400> SEQUENCE: 3
atgggcacac gactc                                                15

<210> SEQ ID NO 4
<211> LENGTH: 5
<212> TYPE: PRT
<213> ORGANISM: Homo sapiens

<400> SEQUENCE: 4

Met Gly Thr Arg Ile
1               5

<210> SEQ ID NO 5
<211> LENGTH: 5
<212> TYPE: DNA
<213> ORGANISM: Artificial Sequence
<220> FEATURE:
<223> OTHER INFORMATION: modified human nucleic acid

```
<400> SEQUENCE: 5 atgac                                                                 5

<210> SEQ ID NO 6
<211> LENGTH: 5
<212> TYPE: DNA
<213> ORGANISM: Artificial Sequence
<220> FEATURE:
<223> OTHER INFORMATION: modified human nucleic acid

<400> SEQUENCE: 6 ataaa                                                                 5

<210> SEQ ID NO 7
<211> LENGTH: 8
<212> TYPE: DNA
<213> ORGANISM: Artificial Sequence
<220> FEATURE:
<223> OTHER INFORMATION: modified human nucleic acid

<400> SEQUENCE: 7 atgatgac                                                              8

<210> SEQ ID NO 8
<211> LENGTH: 8
<212> TYPE: DNA
<213> ORGANISM: Artificial Sequence
<220> FEATURE:
<223> OTHER INFORMATION: modified human nucleic acid

<400> SEQUENCE: 8 atgatgag                                                              8

<210> SEQ ID NO 9
<211> LENGTH: 13
<212> TYPE: DNA
<213> ORGANISM: Artificial Sequence
<220> FEATURE:
<223> OTHER INFORMATION: modified human nucleic acid

<400> SEQUENCE: 9
atgactctga ctc                                                       13

<210> SEQ ID NO 10
<211> LENGTH: 13
<212> TYPE: DNA
<213> ORGANISM: Artificial Sequence
<220> FEATURE:
<223> OTHER INFORMATION: modified human nucleic acid

<400> SEQUENCE: 10
ataaatctaa atc                                                       13
```